United States Patent

Dickinson et al.

Patent Number: 5,457,118
Date of Patent: Oct. 10, 1995

[54] PYRIDINE DERIVED AGENTS FOR CARDIOVASCULAR DISEASES

[75] Inventors: Roger P. Dickinson; Kevin N. Dack; John Steele, all of Sandwich, United Kingdom

[73] Assignee: Pfizer Inc., New York, N.Y.

[21] Appl. No.: 133,155

[22] PCT Filed: Mar. 17, 1992

[86] PCT No.: PCT/EP92/00591

§ 371 Date: Apr. 20, 1994

§ 102(e) Date: Apr. 20, 1994

[87] PCT Pub. No.: WO92/17451

PCT Pub. Date: Oct. 15, 1992

[30] Foreign Application Priority Data

Apr. 4, 1991 [GB] United Kingdom ............... 9107043

[51] Int. Cl.⁶ .............. A61K 31/44; C07D 213/55; C07D 213/70; C07D 213/75

[52] U.S. Cl. ............. 514/345; 514/347; 514/357; 514/343; 514/318; 514/332; 514/336; 514/337; 546/293; 546/294; 546/273; 546/281; 546/194; 546/264; 546/266; 546/283; 546/334; 546/336; 546/338; 546/342

[58] Field of Search ............... 546/293, 294, 546/338, 194, 334, 336, 281, 283, 273, 264, 266, 342; 514/318, 357, 332, 336, 337, 343, 345, 347

[56] References Cited

U.S. PATENT DOCUMENTS

4,837,333  6/1989  Manley et al. ............... 548/341

FOREIGN PATENT DOCUMENTS

2016646  5/1990  Canada.
153678   2/1985  European Pat. Off..
397044   5/1990  European Pat. Off..
405391   6/1990  European Pat. Off..

*Primary Examiner*—Alan L. Rotman
*Attorney, Agent, or Firm*—Peter C. Richardson; Gregg C. Benson; A. Dean Olson

[57] ABSTRACT

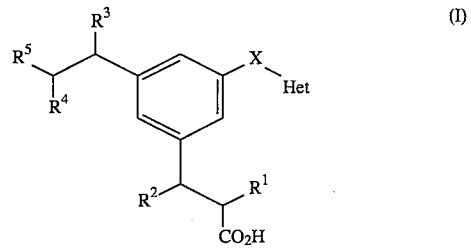

Compounds of formula (I) or a biolabile ester thereof, or a pharmaceutically acceptable salt of either, wherein $R^1$, $R^2$, $R^3$ and $R^4$ are each independently selected from H or $C_1$–$C_4$ alkyl; $R^5$ is $(CH_2)_m SO_2 R^6$, $(CH_2)_m NHSO_2 R^6$ or $(CH_2)_m NHCOR^7$; $R^6$ and $R^7$ are $C_1$–$C_6$ alkyl, $C_1$–$C_3$ perfluoroalkyl$(CH_2)_n$, $C_3$–$C_6$ cycloalkyl$(CH_2)_n$, aryl$(CH_2)_n$ or heteroaryl$(CH_2)_n$; or $R^6$ is $NR^8 R^9$; $R^8$ is H or $C_1$–$C^4$ alkyl; $R^9$ is $C_1$–$C_6$ alkyl, $C_3$–$C_6$ cycloalkyl$(CH_2)_n$, aryl$(CH_2)_n$ or heteroaryl$(CH_2)_n$; or $R^8$ and $R^9$ together with the nitrogen atom to which they are attached form a 5- to 7-membered heterocyclic ring which may optionally incorporate a carbon-carbon double bond or a further hetero atom linkage selected from O, S, NH, $N(C_1$–$C_4$ alkyl) and $N(C_1$–$C_5$ alkanoyl), and which may optionally be substituted with one to three substituents each independently selected from $C_1$–$C_4$ alkyl and $C_1$–$C_4$ alkoxy, and which may optionally be benzo-fused; X is $CH_2$, $CHCH_3$, $C(OH)CH_3$, $C=CH_2$ or O; m is 0 or 1; n is 0, 1, 2 or 3; and Het is 3- or 4-pyridyl or 1-imidazolyl; with the proviso that when Het is 1-imidazolyl then X is $CH_2$ or $CHCH_3$, are combined thromboxane $A_2$ synthetase inhibitors and thromboxane $A_2$/endoperoxide antagonists of utility in the treatment of disease conditions in which thromboxane $A_2$ is a causative agent.

7 Claims, No Drawings

PYRIDINE DERIVED AGENTS FOR CARDIOVASCULAR DISEASES

This application is a §371 of PCT/EP92/00591, which was filed on Mar. 17, 1992.

This invention relates to certain substituted phenoxypyridines, benzylpyridines and benzylimidazoles. Such compounds are able to selectively inhibit the thromboxane $A_2$ synthetase enzyme and antagonise the thromboxane $A_2$/endoperoxide receptor without significantly inhibiting the action of the prostacyclin synthetase or cyclo-oxygenase enzymes. The compounds are thus useful as therapeutic agents, for example in the treatment of atherosclerosis and unstable angina and for prevention of reocclusion post-percutaneous transluminal coronary and femoral angioplasty. They may also find clinical utility in a further variety of disease conditions in which thromboxane $A_2$ has been implicated such as in the treatment of myocardial infarction, stroke, cardiac arrhythmias, transient ischaemic attack, tumour metastasis, peripheral vascular disease, bronchial asthma, renal disease, cyclosporin-induced nephrotoxicity, renal allograft rejection, vascular complications of diabetes and endotoxin shock, and in coronary artery bypass surgery and haemodialysis.

The compounds of the invention are of formula:

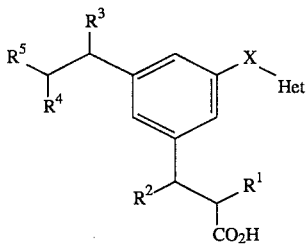

(I)

and include biolabile esters thereof and pharmaceutically acceptable salts both of (I) and of the said biolabile esters, wherein $R^1$, $R^2$, $R^3$ and $R^4$ are each independently selected from H or $C_1$–$C_4$ alkyl; $R^5$ is $(CH_2)_m SO_2 R^6$, $(CH_2)_m NHSO_2 R^6$ or $(CH_2)_m NHCOR^7$; $R^6$ and $R^7$ are each $C_1$–$C_6$ alkyl, $C_1$–$C_3$ perfluoroalkyl$(CH_2)_n$, $C_3$–$C_6$ cycloalkyl $(CH_2)_n$, aryl$(CH_2)_n$ or heteroaryl$(CH_2)_n$;

or $R^6$ is $NR^8 R^9$; $R^8$ is H or $C_1$–$C_4$ alkyl; $R^9$ is $C_1$–$C_6$ alkyl, $C_3$–$C_6$ cycloalkyl$(CH_2)_n$, aryl$(CH_2)_n$ or heteroaryl$(CH_2)_n$;

or $R^8$ and $R^9$ together with the nitrogen atom to which they are attached form a 5- to 7-membered heterocyclic ring which may optionally incorporate a carbon-carbon double bond or a further heteroatom linkage selected from O, S, NH, N($C_1$–$C_4$ alkyl) and N($C_1$–$C_5$ alkanoyl), and which may optionally be substituted with one to three substituents each independently selected from $C_1$–$C_4$ alkyl and $C_1$–$C_4$ alkoxy, and which may optionally be benzo-fused; X is $CH_2$, $CHCH_3$, $C(OH)CH_3$, $C=CH_2$ or O; m is 0 or 1; n is 0, 1, 2 or 3;

and Het is 3- or 4-pyridyl or 1-imidazolyl;

with the proviso that when Het is 1-imidazolyl then X is $CH_2$ or $CHCH_3$.

In the above definition aryl means phenyl or naphthyl, and heteroaryl means furyl, thienyl or pyridyl, any of which ring systems may optionally be substituted with one to three substituents each independently chosen from $C_1$–$C_4$ alkyl, $C_1$–$C_4$ alkoxy, halo, $CF_3$, OH, $OCF_3$ and CN, with the proviso that no heteroaryl ring system is substituted with OH. Unless otherwise indicated, alkyl and alkoxy groups having three or more carbon atoms may be straight-chain or branched-chain. Halo means fluoro, chloro, bromo or iodo.

Compounds containing asymmetric centres can exist as enantiomers and diastereoisomers, and the invention includes the separated individual isomers as well as mixtures of isomers.

Also included in the invention are radiolabelled derivatives of compounds of formula (I) which are suitable for biological studies.

The term biolabile ester in the above definition means a pharmaceutically acceptable, biologically degradable ester derivative of a compound of formula (I), that is a prodrug which, upon administration to an animal or human being, is converted in the body to a compound of formula (I).

In the case of the compounds of formula (I), such biolabile ester prodrugs are particularly advantageous in providing compounds of formula (I) suitable for oral administration. The suitability of any particular ester-forming group can be assessed by conventional in vivo animal or in vitro enzyme hydrolysis studies. Thus desirably, for optimum effect, the ester should only be hydrolysed after absorption is complete. Accordingly, the ester should be resistant to premature hydrolysis by digestive enzymes before absorption, but should be productively hydrolysed by, for example, gut-wall, plasma or liver enzymes. In this way, the active acid is released into the bloodstream following oral absorption of the prodrug.

Suitable biolabile esters may include alkyl, alkanoyloxyalkyl, cycloalkanoyloxyalkyl, aroyloxyalkyl and alkoxycarbonyloxyalkyl esters, including cycloalkyl and aryl substituted derivatives thereof, aryl esters and cycloalkyl esters, wherein said alkyl, alkanoyl or alkoxy groups may contain from 1 to 8 carbon atoms and be branched-chain or straight-chain, said cycloalkyl groups may contain from 3–7 carbon atoms and said cycloalkanoyl groups from 4–8 carbon atoms wherein both are optionally benzo-fused, and said aryl and aroyl groups include substituted phenyl, naphthyl or indanyl ring systems.

Preferably, the biolabile esters of the invention are $C_1$–$C_4$ alkyl esters. More preferably, they are methyl, ethyl and t-butyl esters.

The pharmaceutically acceptable salts of the compounds of formula (I) are those formed with bases or acids which provide non-toxic salts. Examples of the former include the alkali and alkaline earth metal salts such as the sodium, potassium or calcium salts, and salts with amines such as diethylamine. Examples of pharmaceutically acceptable acid addition salts include the hydrochloride, hydrobromide, sulphate or bisulphate, phosphate or hydrogen phosphate, acetate, benzoate, succinate, fumarate, maleate, lactate, citrate, tartrate, gluconate, methanesulphonate, benzenesulphonate and p-toluenesulphonate.

A preferred group of compounds of formula (I) is that wherein $R^1$, $R^2$, $R^3$ and $R^4$ are each independently selected from H or methyl; $R^5$ is $CH_2SO_2$phenyl, $SO_2$phenyl, $NHCOCH_2CH(CH_3)_2$, NHCOphenyl, $CH_2NHSO_2$(4-chlorophenyl) or $NHSO_2 R^6$; $R^6$ is $C_1$–$C_5$ alkyl, $CH_2CF_3$, cyclohexyl, phenyl, 4-fluorophenyl, 4-chlorophenyl, 4-bromophenyl, 4-methylphenyl, 2-furyl or $NR^8 R^9$; $R^8$ is H, methyl or ethyl; $R^9$ is methyl, ethyl or 4-chlorophenyl; or $R^8$ and $R^9$ together with the nitrogen atom to which they are attached form a 1-pyrrolidinyl, 1-(2,5-dihydro)pyrrolyl, piperidino, 1-(1,2,3,6-tetrahydro)pyridyl, 1-(4-methyl-1,2,3,6-tetrahydro)pyridyl or 2-isoindolinyl group; and X and Het are as previously defined; with the proviso that when Het is 1-imidazolyl then X is $CH_2$ or $CHCH_3$.

A particularly preferred group of compounds of formula (I) is that wherein $R^1$, $R^2$, $R^3$ and $R^4$ are H; $R^5$ is $NHSO_2 R^6$;

$R^6$ is phenyl, 4-chlorophenyl or 4-bromophenyl; Het is 3-pyridyl; and X is as previously defined.

In another aspect the present invention provides processes for the preparation of compounds of formula (I), biolabile esters thereof, and pharmaceutically acceptable salts of either.

The compounds of formula (I) are obtained by hydrolysis of their lower alkyl ester precursors of formula (II):

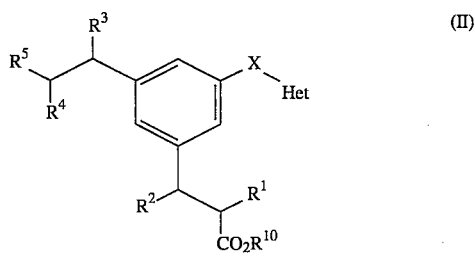

(II)

wherein $R^1$, $R^2$, $R^3$, $R^4$, $R^5$, X and Het are as previously defined for formula (I) and $R^{10}$ is $C_1$–$C_4$ alkyl, preferably methyl, ethyl or t-butyl.

The reaction can be conducted under basic or acidic conditions, e.g. with excess aqueous alkali metal hydroxide solution, preferably sodium hydroxide solution, or excess hydrochloric acid respectively, optionally with a suitable co-solvent such as a $C_1$–$C_4$ alkanol, preferably methanol, at from about 20° C. to the reflux temperature of the reaction medium.

Depending on the nature of $R^5$, X and Het, compounds of formula (II) can be obtained in a variety of ways as exemplified below.

(A) When $R^5$ is $(CH_2)_m NHSO_2 R^6$ or $(CH_2)_m NHCO^7$, wherein $R^6$, $R^7$ and m are as previously defined for formula (I), and either X is $CH_2$, $C(OH)CH_3$ or O and Het is 3- or 4-pyridyl, or X is $CH_2$ or $CHCH_3$ and Het is 1-imidazolyl, such compounds of formula (II) may be obtained by sulphonylation/sulphamoylation or acylation respectively of an amine of formula (III):

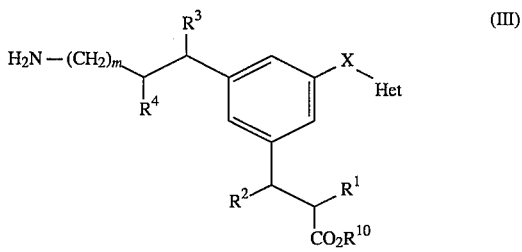

(III)

wherein either X is $CH_2$, $C(OH)CH_3$ or O and Het is 3- or 4-pyridyl, or X is $CH_2$ or $CHCH_3$ and Het is 1-imidazolyl, m is 0 or 1, and $R^1$, $R^2$, $R^3$, $R^4$ and $R^{10}$ are as previously defined for formula (II). The sulphonylation can be carried out by reacting an amine of formula (III) with a sulphonic anhydride of formula $(R^6 SO_2)_2 O$ or a sulphonyl halide (preferably chloride) of formula $R^6 SO_2$halo, wherein halo and $R^6$ are as previously defined with the proviso that $R^6$ is not $NR^8 R^9$. The sulphamoylation is effected in like manner by reaction of (III) with a sulphamoyl halide (preferably chloride) of formula $R^8 R^9 NSO_2$halo, wherein halo, $R^8$ and $R^9$ are as previously defined. For the acylation, either the appropriate acid anhydride of formula $(R^7 CO)_2 O$ or acyl halide (preferably chloride) of formula $R^7 CO$halo, wherein halo and $R^7$ are as previously defined, is employed. These reactions are generally conducted in the presence of excess tertiary amine such as triethylamine, 4-dimethylaminopyridine (DMAP) or pyridine to act as acid scavenger, optionally in the presence of DMAP as catalyst when it is not used as acid scavenger, in a suitable solvent such as dichloromethane, at from about −75° to about 40° C. Alternatively, pyridine can be used to act as both acid scavenger and solvent.

When $R^5$ is $(CH_2)_m NHSO_2 R^6$ or $(CH_2)_m NHCO^7$, wherein $R^6$, $R^7$ and m are as previously defined for formula (I), X is $CHCH_3$ and Het is 3- or 4-pyridyl, such compounds of formula (II) are obtainable by reduction of the corresponding compound of formula (II) wherein X is $C=CH_2$. This may be achieved by catalytic hydrogenation using a palladium on charcoal catalyst in a suitable solvent such as ethanol at about 20° C. and 50 p.s.i. (3.45 bar).

When $R^5$ is $(CH_2)_m NHSO_2 R^6$ or $(CH_2)_m NHCO^7$, wherein $R^6$, $R^7$ and m are as previously defined for formula (I), X is $C=CH_2$ and Het is 3- or 4-pyridyl, such compounds of formula (II) may, in turn, be synthesised by dehydration of the corresponding compound of formula (II) wherein X is $C(OH)CH_3$, by treating this tertiary alcohol with an acid such as trifluoroacetic acid at about 50° C.

The above compounds of formulae (II) and (III) also form part of the invention. The former may be active in vivo by virtue of esterase-mediated hydrolysis to liberate the corresponding acid of formula (I), whilst the latter are key intermediates.

Compounds of formula (III), wherein m is 0 and $R^1$, $R^2$, $R^3$, $R^4$, $R^{10}$, X and Het are as previously defined for formula (III), may be obtained from the corresponding carbamates of formula (IV):

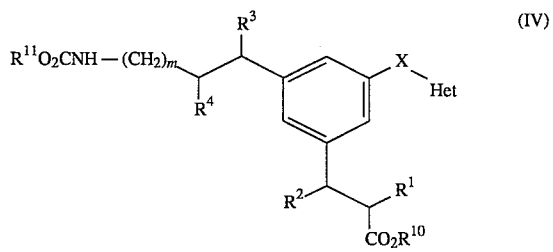

(IV)

wherein $R^{11}$ is a group, e.g. benzyl or t-butyl, which can be selectively removed in the presence of $R^{10}$, m is 0, and $R^1$, $R^2$, $R^3$, $R^4$, $R^{10}$, X and Het are as previously defined for formula (III). When $R^{11}$ is benzyl, amine deprotection is preferably effected by catalytic transfer hydrogenation of the substrate using ammonium formate and palladium on charcoal catalyst in a suitable solvent, e.g. a methanol-tetrahydrofuran mixture, at the reflux temperature of the reaction medium. Alternatively, when $R^{11}$ is t-butyl, either hydrogen chloride or trifluoroacetic acid in a suitable solvent, e.g. dichloromethane, at from about 0° to about 20° C., can be used to achieve the required deprotection.

Compounds of formula (IV), wherein m is 0 and $R^1$, $R^2$, $R^3$, $R^4$, $R^{10}$, $R^{11}$, X and Het are as previously defined for formula (IV), can be synthesised directly, in a one-pot process, from the carboxylic acids of formula (Va):

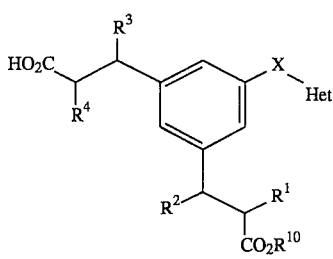

(Va)

wherein $R^1$, $R^2$, $R^3$, $R^4$, $R^{10}$, X and Het are as previously defined for formula (IV). The reaction is carried out by heating, under reflux, a solution of a compound of formula (Va), an "azide-transfer reagent" such as diphenylphosphoryl azide, a tertiary amine such as triethylamine and excess of the, required alcohol, e.g. benzyl alcohol or t-butanol, of formula $R^{11}OH$, in an inert solvent such as 1,4-dioxane; alternatively, the excess alcohol may itself suffice as a suitable solvent. In the first phase of the reaction the acyl azide derivative of (Va) is produced which, under the reaction conditions, undergoes a Curtius rearrangement to generate the intermediate isocyanate. The latter is then trapped in situ by the attendant benzyl alcohol or t-butanol to afford either the benzyl or t-butyl carbamate respectively of formula (IV).

In cases where, for example, $R^{10}$ is methyl or ethyl, the monoacid intermediates of formula (Va) are obtainable from diesters of formula (VIa):

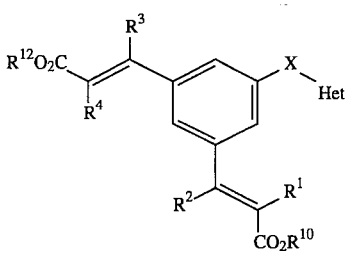

(VIa)

wherein $R^{12}$ is a group, for example t-butyl, which can be selectively removed in the presence of $R^{10}$, $R^{10}$ is methyl or ethyl, and $R^1$, $R^2$, $R^3$, $R^4$, X and Het are as previously defined for formula (Va).

Prior to this selective ester deprotection, the two alkenyl groups are concurrently reduced, preferably by catalytic transfer hydrogenation, which may be effected using the conditions described above for the conversion of IV to III when $R^{11}$ is benzyl, but preferably at a temperature of about 60° C. This step is followed by removal of the t-butyl group ($R^{12}$) using, for example, hydrogen chloride or trifluoroacetic acid at from about 0° to about 20° C. in a solvent such as dichloromethane. Clearly, in cases where $R^{12}$ is benzyl, reduction of the two alkenyl groups and removal of $R^{12}$ is achievable in one step under catalytic transfer hydrogenation conditions.

In cases where, for example, $R^{10}$ is t-butyl, (Va) can be obtained from (VIa) by again ensuring that $R^{12}$ can be selectively removed in the presence of $R^{10}$, e.g. where $R^{12}$ is methyl or ethyl. Thus, after reduction of the two alkenyl groups, base hydrolysis under mild conditions is effected using, for example, about one equivalent of an inorganic base such as sodium hydroxide or potassium hydroxide in aqueous 1,4-dioxane as solvent at from about 20° to about 100° C.

In an alternative approach, compounds of the formula (IV) wherein $R^1=R^4$ and $R^2=R^3$, and $R^{10}$, $R^{11}$, X, m and Het are as previously defined for formula (IV), may be synthesised from monoacids of formula (Vb):

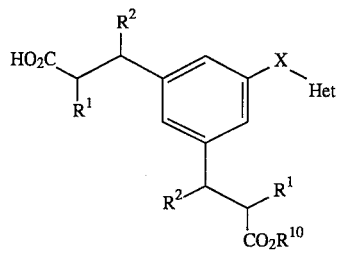

(Vb)

wherein $R^1$, $R^2$, $R^{10}$, X and Het are as previously defined for formula (IV), by processes analogous to those described above for the conversion of (Va) to (IV). The monoacids of formula (Vb) are also obtained in a two-step procedure from the symmetrical unsaturated diesters of formula (VIb):

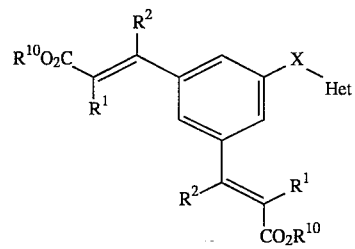

(VIb)

wherein $R^1$, $R^2$, $R^{10}$, X and Het are as previously defined for formula (Vb), by catalytic transfer hydrogenation, as described previously, followed by selective ester deprotection, preferably via base hydrolysis using, for example, about one equivalent of inorganic base such as sodium hydroxide or potassium hydroxide in aqueous solution together with an appropriate co-solvent, at from about 20° C. to the reflux temperature of the reaction medium.

Clearly, this alternative approach is also applicable in cases where $R^1=R^2=R^3=R^4$.

Compounds of formula (III), wherein m is 1 and $R^1$, $R^2$, $R^3$, $R^4$, $R^{10}$, X and Het are as previously defined for formula (III), may be obtained by direct reduction of compounds of formula (VIc):

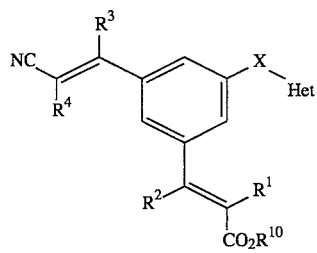

(VIc)

wherein $R^1$, $R^2$, $R^3$, $R^4$, $R^{10}$, X and Het are as previously defined for formula (III). The one-step reduction of the nitrile group and both alkenyl groups of (VIc) may be achieved by a cobalt(II)-mediated process, in which a mixture of cobalt(II) chloride, sodium borohydride and the substrate of formula (VIc), in a suitable solvent, e.g. ethanol, is allowed to react at about 0° C.

Compounds of formula (VIa) may be obtained by a variety of synthetic procedures, depending on the nature of X and Het. For example, when X is $CH_2$, $C(OH)CH_3$ or O and Het is 3- or 4-pyridyl, and $R^1$, $R^2$, $R^3$, $R^4$, $R^{10}$ and $R^{12}$ are as previously defined for formula (VIa), they may be obtained from alkenoic esters of formula (VII):

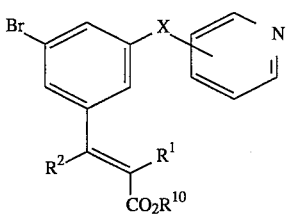

wherein X is $CH_2$, $C(OH)CH_3$ or O, and $R^1$, $R^2$ and $R^{10}$ are as previously defined for formula (VIa), using standard Heck reaction methodology. This involves treatment of (VII) with excess alkenoic ester of formula (VIII).

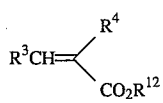

wherein $R^3$, $R^4$ and $R^{12}$ are as previously defined for formula (VIa), in the presence of palladium(II) acetate, tri-o-tolylphosphine and triethylamine, in a suitable solvent such as acetonitrile or dimethylformamide, at from about 80° to about 160° C.

The alkenoic esters of formula (VII) can be synthesised by reaction, at from about 20° to about 100° C., of the appropriate aldehyde or ketone of formula (IX):

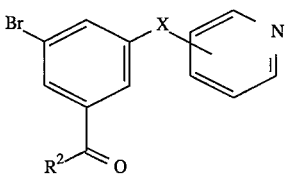

wherein $R^2$ and X are as previously defined for formula (VII), with a phosphonate of formula (X):

wherein $R^{13}$ is $C_1$–$C_4$ alkyl, preferably methyl or ethyl, and $R^1$ and $R^{10}$ are as defined for formula (VII). The intermediate phosphorous ylid is generated in situ from (X) using a base such as sodium hydride in a suitable dry solvent, e.g. tetrahydrofuran, 1,2-dimethoxyethane or dimethylformamide.

Compounds of formula (IX) are obtainable from the corresponding dibromoarene precursors of formula (XI):

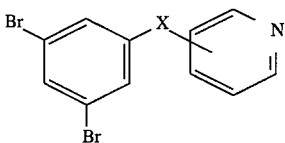

wherein X is as previously defined for formula (IX), as follows: (i) monobromo-lithium exchange using s-butyllithium in dry ether-hexane as solvent at about −70° C., and (ii) acylation of the resulting aryllithium with the appropriate tertiary amide, e.g. a N,N-dimethylalkanoamide of formula $R^2CON(CH_3)_2$, at from about −70° to about 0° C., Compounds of formula (XI) may be derived from 1,3,5-tribromobenzene by one of three different procedures. For example, when X is $CH_2$, as follows: (i) monobromo-lithium exchange using n-butyllithium in dry ether-hexane at about −70° C., (ii) reaction of the resulting 3,5-dibromophenyllithium with either 3- or 4-cyanopyridine as required at from about −70° to about 0° C., and (iii) quenching and hydrolysis of the intermediate lithium-imine salt with hydrochloric acid at from about 0° to about 100° C. These three steps afford the ketone precursors of (XI), i.e. compounds of formula (XI) wherein X is C=O, which are reduced under typical Wolff-Kishner (Huang-Minlon modification) conditions, viz. hydrazine hydrate followed by potassium hydroxide in refluxing ethylene glycol.

When X is $C(OH)CH_3$, compounds of formula (XI) may be synthesised by reaction of 3,5-dibromophenyllithium (prepared as indicated above) with either 3- or 4-acetylpyridine at from about −70° to about 0° C.

When X is O, compounds of formula (XI) are obtainable by reaction of 1,3,5-tribromobenzene with the anion of either 3- or 4-hydroxypyridine, generated using a base such as sodium hydride, in the presence of cuprous oxide in a suitable solvent, e.g. collidine, at about 200° C. Alternatively these compounds may be obtained from the anion of 3,5-dibromophenol and a 3- or 4-halopyridine, wherein halo is preferably bromo.

It will be apparent to persons skilled in the art that the order of the steps involved in converting (XI) to (VIa) may be varied. For example, (XI) may be subjected to a Heck reaction with an alkenoic ester of formula (XII):

wherein $R^1$, $R^2$ and $R^{10}$ are as previously defined for formula (VIa), to provide (VII), followed by bromo-lithium exchange and acylation of (VII) with, for example, a tertiary amide of formula $R^3CON(CH_3)_2$ to give an aldehyde or ketone of formula (XIII):

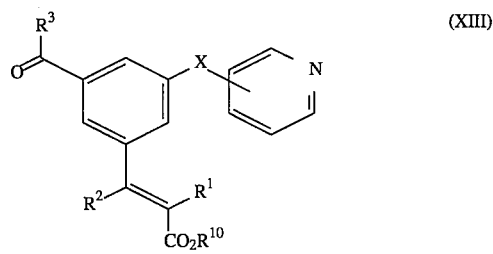

wherein $R^1$, $R^2$, $R^3$, $R^{10}$ and X are as previously defined for formula (VIa). Finally, (XIII) is subjected to standard Wittig-Horner chemistry using a phosphonate such as that of formula (XIV):

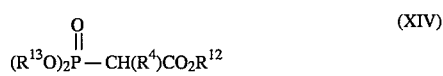

wherein $R^{13}$ is $C_1$–$C_4$ alkyl, preferably methyl or ethyl, and $R^4$ and $R^{12}$ are as previously defined for formula (VIa).

Alternatively (XI) may be converted to (VIa) by subjecting (IX) to a Heck reaction with (VIII) followed by Wittig-Horner reaction of the resulting acylarylalkenoate with (X).

Compounds of formula (VIa), wherein X is $CH_2$ or $CHCH_3$, Het is 1-imidazolyl, and $R^1$, $R^2$, $R^3$, $R^4$, $R^{10}$ and $R^{12}$ are as defined for formula (VIa), may be obtained from benzyl alcohols of formula (XV):

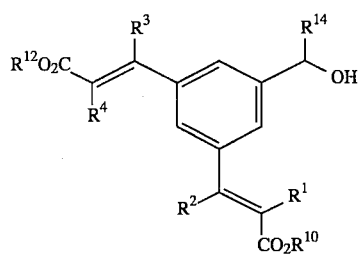

(XV)

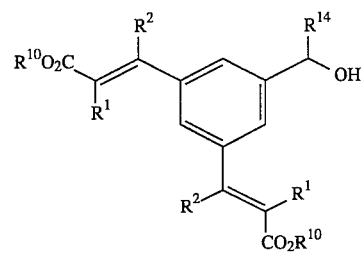

(XVI)

wherein $R^{14}$ is H or $CH_3$, and $R^1$, $R^2$, $R^3$, $R^4$, $R^{10}$ and $R^{12}$ are as previously defined for formula (VIa), by activation of the alcohol function towards nucleophilic displacement by imidazole, e.g. by mesylation. Thus treatment of (XV) with methylsulphonyl chloride in the presence of a tertiary amine, e.g. triethylamine, in a solvent such as dichloromethane at from about 0° to about 20° C. provides the intermediate mesylate which is then reacted, conveniently without isolation and characterisation, with imidazole, preferably in the presence of a base, e.g. sodium carbonate, and a catalytic amount of sodium iodide or potassium iodide in a solvent such as acetone at from about 20° C. to the reflux temperature of the reaction medium.

Compounds of formula (XV), wherein $R^{14}$ is H, and $R^1$, $R^2$, $R^3$, $R^4$, $R^{10}$ and $R^{12}$ are as previously defined for formula (VIa), may be obtained from 3,5-dibromobenzyl alcohol by processes analogous to those described above for the conversion of (XI) to (VIa). 3,5-Dibromobenzyl alcohol can be obtained by standard reduction procedures, e.g. by using sodium borohydride in methanol as solvent at from about 0° to about 20° C., from 3,5-dibromobenzaldehyde which, in turn, is accesible from 1,3,5-tribromobenzene via 3,5-dibromophenyllithium and subsequent formylation as previously described. Alternatively, 3,5-dibromobenzyl alcohol may be synthesised directly from 1,3,5-tribromobenzene by treating the derived 3,5-dibromo-phenyllithium with either gaseous formaldehyde or paraformaldehyde.

Compounds of formula (XV), wherein $R^{14}$ is $CH_3$, and $R^1$, $R^2$, $R^3$, $R^4$, $R^{10}$ and $R^{12}$ are as previously defined for formula (VIa), are similarly obtainable from α-methyl-3,5-dibromobenzyl alcohol which, in turn, may also be obtained via 3,5-dibromophenyllithium either by reaction with acetaldehyde or by acetylation using, for example, dimethylacetamide, followed by conversion of the resulting acetophenone with a reducing agent such as sodium borohydride.

Compounds of formula (VIb) may also be obtained by a variety of synthetic procedures, depending on the nature of X and Het. For example, when X is $CH_2$, $C(OH)CH_3$ or O and Het is 3- or 4-pyridyl, and $R^1$, $R^2$ and $R^{10}$ are as previously defined for formula (VIb), they may be obtained from (XI) via a "double Heck reaction" using the required excess of alkenoate (XII) under conditions previously described. When Het is 1-imidazolyl and X is $CH_2$ or $CHCH_3$, the "double Heck reaction" with (XII) is applied to 3,5-dibromobenzyl alcohol to furnish compounds of formula (XVI):

wherein $R^{14}$ is H or $CH_3$, and $R^1$, $R^2$ and $R^{10}$ are as previously defined for formula (VIb). The alcohol group is then converted to a 1-imidazolyl group by procedures already summarised.

Compounds of formula (VIc) may be obtained by procedures completely analogous to those described for the generation of (VIa) and (VIb), by employing the appropriate α,β-unsaturated nitrile for the Heck reaction or the appropriate cyanoalkylphosphonate for the Wittig-Horner reaction. These procedures are similarly applicable to compounds of formula (VIc) wherein $R^1=R^4$ and $R^2=R^3$.

(B) When $R^5$ is $(CH_2)_mSO_2R^6$, wherein $R^6$ and m are as previously defined for formula (I), and either X is $CH_2$, $C(OH)CH_3$ or O and Het is 3- or 4-pyridyl, or X is $CH_2$ or $CHCH_3$ and Het is 1-imidazolyl, compounds of formula (II) may be obtained from a compound of formula (XVII):

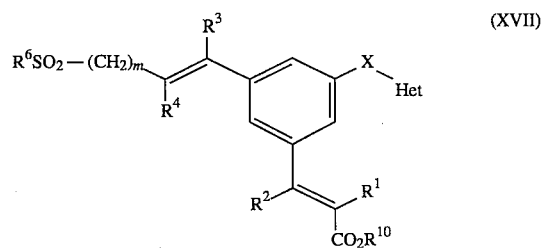

(XVII)

wherein either X is $CH_2$, $C(OH)CH_3$ or O and Het is 3- or 4-pyridyl, or X is $CH_2$ or $CHCH_3$ and Het is 1-imidazolyl, and $R^1$, $R^2$, $R^3$, $R^4$ and $R^{10}$ are as previously defined for formula (II), and $R^6$ and m are as previously defined for formula (I), by reduction of the two alkenyl groups, preferably concurrently and preferably using diimide. This can be achieved by employing up to about a ten-fold excess of 4-methylphenylsulphonyl hydrazine in a suitable solvent such as toluene at the reflux temperature of the reaction medium.

When $R^5$ is $(CH_2)_mSO_2R^6$, wherein $R^6$ and m are as previously defined for formula (I), X is either $C=CH_2$ or $CHCH_3$ and Het is 3- or 4-pyridyl, such compounds of formula (II) are obtained sequentially from the corresponding compound of formula (II) wherein X is $C(OH)CH_3$ by analogy with processes described earlier for the corresponding compounds in which $R^5$ is either $(CH_2)_mNHSO_2R^6$ or $(CH_2)_mNHCOR^7$.

The compounds of formula (XVII), which as key intermediates also form part of the invention, are obtainable by procedures completely analogous to those described for the generation of (VIa), by employing the appropriate vinylic or allylic sulphone/sulphonamide for the Heck reaction or the appropriate sulphonylalkylphosphonate or sulphamoylalkylphosphonate for the Wittig-Horner reaction. These procedures are similarly applicable to compounds of formula (XVII) wherein $R^1=R^4$ and $R^2=R^3$.

The alkenoic esters of formulae (VIII) and (XII), the phosphonates of formulae (X) and (XIV), the α,β-unsaturated nitriles or cyanoalkylphosphonates required for compounds of formula (VIc), the vinylic or allylic sulphones and sulphonamides or the sulphonylalkylphosphonates and sulphamoylalkylphosphonates required for compounds of formula (XVII), and the sulphonyl halides, sulphamoyl halides, acyl halides and acid anhydrides required in the previously described processes, when neither commercially available nor subsequently described, can be obtained by conventional synthetic procedures, in accordance with literature precedent, from readily accessible starting materials using appropriate reagents and reaction conditions.

Persons skilled in the art will recognise that the alkenes depicted hereinbefore may be obtained in alternative geometrically isomeric forms, or as mixtures of geometrical isomers, and are represented in one such form only in the interests of clarity and convenience.

Alternative biolabile esters to those hereinbefore defined by formula (II) may be obtained from the acids of formula (I) by standard reactions. For example, aryl and alkyl esters can be synthesised via activation of the carboxylic acid group of (I) in a variety of ways, such as by forming the acyl chloride, followed by reaction with the required phenol or alcohol. Alternatively, alkyl esters are obtainable by alkylation of a suitable alkali, or alkaline earth, metal carboxylate salt of a compound of formula (I).

The pharmaceutically acceptable acid addition salts of the compounds of formula (I) or their biolabile esters may also be prepared in a conventional manner. For example a solution of the free base is treated with the appropriate acid, either neat or in an appropriate solvent, and the resulting salt isolated either by filtration or by evaporation under vacuum of the reaction solvent. Pharmaceutically acceptable base addition salts of the compounds of formula (I) can be obtained in an analogous manner by treating a solution of a compound of formula (I) with the appropriate base. Both types of salt may be formed or interconverted using ion-exchange resin techniques.

All of the above reactions are entirely conventional and the necessary reagents and conditions for their performance can readily be established by reference to standard text books and to the Examples provided hereafter. Alternatives and variations will also be evident to persons skilled in the art to enable all the compounds defined by formula (I) to be prepared.

As previously mentioned, the compounds of the invention are able to both selectively inhibit the thromboxane $A_2$ synthetase enzyme and also to antagonise the thromboxane $A_2$/endoperoxide receptor.

Thromboxane $A_2$ ($TxA_2$) is a naturally occurring prostanoid which is known to be a potent vasoconstrictor and platelet aggregating agent. $TxA_2$ is also believed to be involved in a number of disease states including atherosclerosis, ischaemic heart disease, peripheral vascular disease and myocardial infarction. $TxA_2$ acts at the thromboxane $A_2$ receptor, at which site other prostanoids, notably prostaglandin $H_2$, may also be agonists.

It is established that the actions of $TxA_2$ may be suppressed in either of two ways. Firstly, an agent which inhibits the generation of $TxA_2$ from $PGH_2$ may be used, i.e. a thromboxane $A_2$ synthetase inhibitor. Secondly, an agent which preferentially occupies but does not activate the $TxA_2$ receptor may be administered, i.e. a thromboxane $A_2$ receptor antagonist.

A potential advantage of the former approach is that accumulated $PGH_2$ substrate may be diverted to produce more of the vasodilator and antiaggregatory $PGI_2$. However, a possible drawback of the approach is that the $PGH_2$ can activate the $TxA_2$ receptor, thus partly eliminating the benefit of suppressing $TxA_2$ formation. Furthermore, if inhibition of $TxA_2$ synthetase is incomplete, sufficient $TxA_2$ may be available to induce some platelet activation.

$TxA_2$ receptor antagonists have the potential advantage over $TxA_2$ synthetase inhibitors of blocking the action of both $TxA_2$ and $PGH_2$ at the $TxA_2$ receptor. However, drawbacks of this class of compound are represented by the competitive nature of their action, which could lead to displacement from receptors by the exceedingly high amounts of $TxA_2$ generated at local sites of platelet activation, and also by the fact that they do not increase the beneficial endogenous PGI formation.

The combination of both $TxA_2$ synthetase inhibitory activity and $TxA_2$ antagonism in the compounds of the present invention provides a solution to the limitations of both classes of compounds. Such compounds will thus suppress the effects of $TxA_2$ and other prostanoids acting at the $TxA_2$ receptor whilst simultaneously promoting elevated levels of $PGI_2$, thus offering a clear advantage over either single agent alone.

The resulting compounds will find utility in the disease states already mentioned as well as those in which $PGD_2$ and $PGF_{2\alpha}$ may be implicated as mediators such as diabetes, bronchial asthma and other inflammatory conditions.

The biological activity of the compounds of the invention has been demonstrated using the following in vitro and in vivo assay procedures:

1. Cyclo-oxygenase

Ram seminal vesicle microsomes (Biochemistry, 1971, 10, 2372) are incubated with arachidonic acid (100.0 µM) for 1.0 minute at 22° C. to produce endoperoxide ($PGH_2$). Aliquots of $PGH_2$ are incubated for 30 seconds at 22° C. with pig aorta microsomes (Nature, 1976, 263, 663) and the reaction terminated with five volumes of ethanol. $PGI_2$ production is assessed by measuring its stable breakdown product 6-keto-$PGF_{1\alpha}$, using a specific radioimmunoassay.

The test compound is pre-incubated with the cyclo-oxygenase source in ram seminal vesicles for 30 minutes at 0° C. The ability of the compound to inhibit $PGH_2$ formation by the enzyme is measured indirectly by evaluation of the 6-keto-$PGF_{1\alpha}$ produced upon addition of $PGI_2$ synthetase (30 seconds at 22° C.).

2. Prostacyclin ($PGI_2$) Synthetase

Pig aorta microsomes (Nature, 1976, 263, 663) are incubated for 30 seconds at 22° C. with $PGH_2$ (produced as in 1) and the reaction terminated with 5 volumes of ethanol. $PGI_2$ production is assessed by measuring its stable breakdown product, 6-keto $PGF_{1\alpha}$, using a specific radioimmunoassay. $PGI_2$ production can be completely inhibited by pre-incubation of the enzyme $PGI_2$ synthetase with the selective $PGI_2$ synthetase inhibitor 15-hydroperoxyarachidonic acid (Prostaglandins, 1976, 12, 715). The test compound is pre-incubated with the enzyme for 5 minutes, and its ability to prevent the production of $PGI_2$ (6-keto-$PGF_{1\alpha}$) is measured.

3. Thromboxane $A_2$ ($TxA_2$) Synthetase

Indomethacin pretreated human platelet microsomes (Science 1976, 193, 163) are incubated for 2 minutes at 0° C. with $PGH_2$ (produced as in 1) and the reaction terminated with 5 volumes of ethanol. $TxA_2$ production is assessed by measuring its stable metabolite $TxB_2$, using a specific radioimmunoassay.

The test compound is pre-incubated with enzyme for 5 minutes, and its ability to inhibit the thromboxane $A_2$ synthetase enzyme is measured as the reduction of $TxA_2$ ($TxB_2$) production.

Compounds of the formula (I) tested in this way have been shown to be capable of selectively inhibiting the thromboxane A$_2$ synthetase enzyme.

4. Thromboxane A$_2$ receptor antagonism

Spirally cut rat aortic strips, mounted for isometric tension recording in 20 ml organ baths, are bathed in Krebs-bicarbonate solution at 37° C. Following an incubation period of 2 hours under 1 gram resting tension, the tissues are pre-treated with U-46619 (a thromboxane A$_2$ receptor agonist) for 10 minutes, then washed and the tissues allowed to equilibrate for a further 1 hour. Cumulative doses of U-46619 over the range 1 nM–100 nM are sequentially included in the bathing fluid and increases in the tissue tension noted.

The test compounds are incubated with the tissue for 15 minutes prior to repeating the cumulative dosing of U-46619 and the ability of the compound to antagonize the thromboxane A$_2$ receptor is determined from the dose-response curves for U-46619 in the presence of varied concentrations of the test compound.

5. Anaesthetised Rabbits

Thromboxane A$_2$ synthetase inhibition and receptor antagonism are evaluated ex vivo in anaesthetised rabbits as follows:

New Zealand White rabbits (2–2.5 kg) are anaesthetised with fentanyl citrate (0.189 mg) and fluanisone (6 mg) intramuscularly and midazolam (3 mg) intravenously and maintained by an intravenous infusion of fentanyl citrate (0.315 mg), fluanisone (1 mg) and midazolam (1 mg) per hour. After cannulation of the trachea, a carotid artery is cannulated for collection of blood samples. The catheter is kept patent by the presence within the catheter of saline containing heparin (50 μ/ml). Control carotid arterial blood samples are taken 25 and 5 minutes prior to administration of the test compound via a marginal ear vein. Two groups of rabbits are used. The first group receives 0.01 mg/kg of the test compound followed, at ten minute intervals, by 0.03, 0.1, 0.3, 1.0, 3.0 and 10 mg/kg; the second group comprises the controls. Carotid arterial blood samples are taken 5 minutes after all doses. At each time point, a 1 ml blood sample is collected in a glass test tube, without anticoagulant, for TxB$_2$ determination. This blood is allowed to clot during a two hour incubation at 37° C. and the serum obtained by centrifugation. Serum samples are then processed through the TxB$_2$ radioimmunoassay after deproteinisation with ethanol.

A further 900 μl blood sample, taken at each time point, is immediately mixed with 100 μl of trisodium citrate (3.15%). After 90 minutes incubation at room temperature, this sample is mixed in equal proportions with an aggregometry buffer (J. Pharmacol. Methods, 1981, 6, 315) and brought to 37° C. Electrodes for the measurement of electrical impedance are placed in the blood and U-46619 (final concentration 3 μM) is added to the blood. Antagonism of platelet thromboxane A$_2$ receptors by the compound is assessed by comparing the change in electrical impedance produced by U-46619 in compound-treated rabbits with the untreated controls. The compounds are also evaluated in vivo using a modified Folt's model as follows:

New Zealand White rabbits (2–2.5 kg) are anaesthetised as described above. After cannulation of the trachea, a carotid artery is exposed, separated from the vagus nerve and the blood flow is monitored by an extraluminal probe. A 3–4 mm section of the artery is gently crushed by artery forceps. A stenosis clip is applied to the artery at the position of the crush injury to limit the blood flow in the artery to 6 ml/min. Cessation of blood flow due to accumulation of platelet deposits within the lumen of the vessel is timed. Blood flow is restored by manual flicking of the clip. The test compound is administered to the animal via a marginal ear vein and responses to the compound are assessed by measuring the reduction in the rate of blood flow decrease due to inhibition of thrombus formation in the vessel.

6. Conscious Dogs

Thromboxane A$_2$ synthetase inhibition and receptor antagonism may also be evaluated ex vivo in sling-restrained conscious dogs after oral (p.o.) or intravenous (i.v.) administration of a compound of the invention. The sampling and assaying procedures employed are similar to those described for the ex vivo anaesthetised rabbit experiments.

For administration to man, in the therapy or prevention of diseases or adverse medical conditions in which TxA$_2$ is implicated as a causative agent, oral dosages of the compounds would be expected to be in the range of from 4–800 mg daily for an average adult patient (70 kg). Thus for a typical adult patient, individual tablets or capsules contain from 2 to 400 mg of active compound, in a suitable pharmaceutically acceptable vehicle or carrier, for administration as a single dose, or in multiple doses, once or several times a day. Dosages for intravenous administration would typically be within the range of from 1 to 400 mg per single dose required. In practice the physician will determine the actual dosage which will be most suitable for an individual patient and it will vary with the age, weight and response of the particular patient, and with the condition being treated. The above dosages are exemplary of the average case but there can, of course, be individual instances where higher or lower dosage ranges are merited, and such are within the scope of this invention.

For human use, the compounds of the formula (I) can be administered alone, but will generally be administered in admixture with a pharmaceutical carrier selected with regard to the intended route of administration and standard pharmaceutical practice. For example, they may be administered orally in the form of tablets containing such excipients as starch or lactose, or in capsules or ovules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other substances, for example enough salts or glucose, to make the solution isotonic with blood.

Thus the invention provides a pharmaceutical composition comprising a compound of formula (I), or a biolabile ester thereof, or a pharmaceutically acceptable salt of either, together with a pharmaceutically acceptable diluent or carrier.

The invention also provides a compound of formula (I), or a biolabile ester thereof, or a pharmaceutically acceptable salt of either, or a pharmaceutical composition containing any of these entities, for use in medicine.

The invention further includes the use of a compound of formula (I), or a biolabile ester thereof, or a pharmaceutically acceptable salt of either, or a pharmaceutical composition containing any of these entities, for the manufacture of a medicament for the treatment of disease conditions in which thromboxane A$_2$ is a causative agent.

In a further aspect, the invention provides a method of treating or preventing disease conditions in which thromboxane A$_2$ is a causative agent in a mammal (including a human being) which comprises administering to said mammal a therapeutically effective amount of a compound of formula (I), or a biolabile ester thereof, or a pharmaceutically acceptable salt of either, or a pharmaceutical composition containing any of these entities.

The invention also includes any novel intermediates disclosed herein such as those of formulae (III) and (XVII).

The synthesis of the compounds of the invention and of the intermediates for use in their preparation are illustrated by the following Examples and Preparations. The purity of the compounds was routinely monitored by thin layer chromatography (TLC) using Merck Kieselgel 60 $F_{254}$ plates and the following solvent systems (SS):
1. dichloromethane:methanol, 95:5.
2. dichloromethane:methanol:0.880 ammonia, 90:10:1.
3. dichloromethane:methanol:0.880 ammonia, 80:20:1.
4. ethyl acetate.
5. dichloromethane:methanol:0.880 ammonia, 100:20:1.
6. dichloromethane:methanol, 90:10.
7. dichloromethane:methanol:glacial acetic acid, 90:10:1.
8. dichloromethane:methanol, 98:2.
9. hexane:ethyl acetate, 1:1.
10. dichloromethane:methanol:0.880 ammonia, 95:5:0.5.

$^1$H-Nuclear magnetic reasonance (NMR) spectra were recorded using either a Nicolet QE-300 or a Bruker AC-300 spectrometer and were in all cases consistent with the proposed structures. Chemical shifts are given in parts-per-million downfield from tetramethylsilane using conventional abbreviations for designation of major peaks: s, singlet; d, doublet; t, triplet; m, multiplet and br, broad.

Mass spectral were obtained using a Kratos Concept-1S mass spectrometer.

EXAMPLE 1

Ethyl 3-[3-(2-phenylsulphonylamino)ethyl-5-(3-pyridylmethyl)phenyl]propanoate

A solution of phenylsulphonyl chloride (0.195 g) in dichloromethane (1 ml) was added dropwise to a stirred solution of ethyl 3-[3-(2-aminoethyl)-5-(3-pyridylmethyl)phenyl]propanoate (Preparation 47; 0.312 g) and triethylamine (0.202 g) in dichloromethane (4 ml) at room temperature. The solution was stirred for 1 hour, washed with water and dried (MgSO$_4$). Evaporation under vacuum of the solution gave an oil which was chromatographed on silica gel. Elution with dichloromethane:methanol (50:1) gave the title compound as an oil (0.45 g); δ (CDCl$_3$): Rf 0.50 (SS 1); 1.21 (3H,t,J=7.1 Hz), 2.54(2H,t,J=7.7 Hz), 2.69(2H,t,J=6.9 Hz), 3.20(2H,m), 3.88(2H,s), 4.09(2H,q,J=7.1 Hz), 4.43(1H, t,J=6.1 Hz), 6.72(1H,s), 6.77(1H,s), 6.87(1H,s), 7.18–7.22(1H,m), 7.41–7.60(4H,m), 7.79–7.81 (2H,m), 8.46(2H,m).

The following twenty four compounds were obtained from their respective amine precursors, using the appropriate sulphonyl chloride, sulphamoyl chloride or acyl chloride, by procedures similar to that described in Example 1. In Examples 14, 15, 16, 17, 22 and 23, acetonitrile rather than dichloromethane was used as reaction solvent.

EXAMPLE 2

Ethyl 3-{3-[2-(4-methylphenylsulphonylamino)ethyl]-5-(3-pyridylmethyl)phenyl}propanoate From Preparation 47 and 4-methylphenylsulphonyl chloride; Rf 0.70 (SS 2). Found: C,66.61; H,6.26; N,5.78. $C_{26}H_{30}N_2O_4S$ requires C,66.92; H,6.48; N,6.01%.

EXAMPLE 3

Ethyl 3-{3-[2-(4-fluorophenylsulphonylamino)ethyl]-5-(3-pyridylmethyl)phenyl}propanoate From Preparation 47 and 4-fluorophenylsulphonyl chloride; Rf 0.60 (SS 2); δ (CDCl$_3$): 1.21(3H,t,J=7.1 Hz), 2.55(2H,t,J=7.7 Hz), 2.70(2H,t,J=6.85 Hz), 2.85(2H,t,J=7.7 Hz), 3.16–3.22(2H,m), 3.88(2H,s), 4.09(2H,q,J=7.1 Hz), 4.50–4.55(1H,m), 6.73(1H,s), 6.79(1H,s), 6.87(1H,s), 7.13–7.23(3H,m), 7.43 (1H,d,J=7.87 Hz), 7.78–7.83(2H,m), 8.45(2H,m).

EXAMPLE 4

Ethyl 3-{3-[2-(4-chlorophenylsulphonylamino)ethyl]-5-(3-pyridylmethyl)phenyl}propanoate From Preparation 47 and 4-chlorophenylsulphonyl chloride; Rf 0.65 (SS 2). Found: C,61.68; H,5.52; N,5.75. $C_{25}H_{27}ClN_2O_4S$ requires C,61.65; H,5.59; N,5.75%.

EXAMPLE 5

Ethyl 3-{3-[2-(4-bromophenylsulphonylamino)ethyl]-5-(3-pyridylmethyl)phenyl}propanoate From Preparation 47 and 4-bromophenylsulphonyl chloride; Rf 0.65 (SS 2). Found: C,56.51; H,5.13; N,5.20. $C_{25}H_{27}BrN_2O_4S$ requires C,56.50; H,5.12; N,5.27%.

EXAMPLE 6

Ethyl 3-{3-[2-(2-furylsulphonylamino)ethyl]-5-(3-pyridylmethyl)phenyl}propanoate From Preparation 47 and 2-furylsulphonyl chloride; Rf 0.75 (SS 3); δ (CDCl$_3$): 1.20(3H,t,J=7.2 Hz), 2.54(2H,t,J= 7.8 Hz), 2.70(2H,t,J=7.0 Hz), 2.85(2H,t,J=7.8 Hz), 3.24–3.31(2H,m), 3.88(2H,s), 4.08(2H,q,J=7.2 Hz), 5.01(1H,t,J=6.0 Hz), 6.47(1H,m), 6.75(1H,s), 6.81(1H,s), 6.86(1H,s), 7.00(1H,d,J=3.3 Hz), 7.17–7.21 (1H,m), 7.42(1H,d,J=7.9 Hz), 7.50(1H,s), 8.41–8.43 (2H,m).

EXAMPLE 7

Ethyl 3-[3-(2-methylsulphonylamino)ethyl-5-(3-pyridylmethyl)phenyl]propanoate

From Preparation 47 and methylsulphonyl chloride; Rf 0.35 (SS 1); δ (CDCl$_3$): 1.18(3H,t,J=7.7 Hz), 2.54(2H,t,J= 7.7 Hz), 2.75–2.87(4H,m), 2.78(3H,s), 3.32(2H,m), 3.88(2H,s), 4.06(2H,q,J=7.7 Hz), 5.02(1H,t,J=6.1 Hz), 6.84(1H,s), 6.86(1H,s), 6.89(1H,s), 7.15–7.19(1H,m), 7.42(1H,d,J=7.8 Hz), 8.38–8.42 (2H,m).

EXAMPLE 8

Ethyl 3-{3-[2-(1-propylsulphonylamino)ethyl]-5-(3-pyridylmethyl)phenyl}propanoate From Preparation 47 and 1-propylsulphonyl chloride; Rf 0.50 (SS 1); δ (CDCl$_3$): 1.00(3H,t,J=7.5 Hz), 1.21(3H,t,J= 7.1 Hz), 1.71–1.78(2H,m), 2.57(2H,t,J=7.7 Hz), 2.80(2H,t, J=6.9 Hz), 2.84–2.92 (4H,m), 3.33(2H,m), 3.92(2H,s), 4.06(1H,m), 4.10(2H,q,J=7.5 Hz), 6.85(1H,s), 6.91(2H,s), 7.19–7.23 (1H,m), 7.45(1H,d,J=7.8 Hz), 8.46–8.48(2H,m).

EXAMPLE 9

Ethyl 3-{3-[2-(2-propylsulphonylamino)ethyl]-5-(3-pyridylmethyl)phenyl}propanoate From Preparation 47 and 2-propylsulphonyl chloride; Rf 0.50 (SS 1); δ (CDCl$_3$): 1.20(3H,t,J=7.2 Hz), 1.27(6H,d,J= 6.8 Hz), 2.56(2H,t,J=7.9 Hz), 2.79(2H,t,J=7.0 Hz), 2.87(2H, t,J=7.9 Hz), 3.06(1H,m), 3.36(2H,m), 3.90(2H,s), 4.08(2H, q,J=7.2 Hz), 4.34(1H,t,J=6.15 Hz), 6.85(1H,s), 6.88(1H,s), 6.91(1H,s), 7.17–7.21(1H,m), 7.43–7.46(1H,m), 8.42–8.46 (2H,m).

EXAMPLE 10

Ethyl 3-{3-(3-pyridylmethyl)-5-[2-(2,2,2-trifluoroethylsulphonylamino)ethyl]phenyl}propanoate From preparation 47 and 2,2,2-trifluoroethylsulphonyl chloride; Rf 0.40 (SS 2). Found: C,54.77; H,5.31; N,6.03. $C_{21}H_{25}F_3N_2O_4S$ requires C,55.01; H,5.50; N,6.11%.

EXAMPLE 11

Ethyl 3-[3-(2-dimethylsulphamoylamino)ethyl-5-(3-pyridylmethyl)phenyl]propanoate From preparation 47 and dimethylsulphamoyl chloride; Rf 0.50 (SS 1); δ (CDCl$_3$) 1.21(3H,t,J=7.1 Hz), 2.57(2H,t, J=7.7 Hz), 2.73(6H,s), 2.77–2.81(2H,m), 2.89(2H,t,J=7.7 Hz), 3.28(2H,m), 3.92(2H,s), 3.97(1H,t,J=6.2 Hz), 4.10(2H, q,J=7.1 Hz), 6.85(1H,s), 6.91(2H,s), 7.19–7.26(1H,m), 8.46–8.48(2H,m).

EXAMPLE 12

Ethyl 3-[3-(2-benzoylamino)ethyl-5-(3-pyridylmethyl)phenyl]propanoate

From preparation 47 and benzoyl chloride; Rf 0.70 (SS 2); δ (CDCl$_3$): 1.17–1.23(3H,m), 2.53–2.59(2H,m), 2.84–2.91(4H,m), 3.63–3.70(2H,m), 3.90(2H,s), 4.04–4.12(2H,m), 6.11(1H,s), 6.89(2H,s), 6.94(1H,s), 7.12–7.18(1H,m), 7.38–7.49(4H,m), 7.67(2H,d,J=7.2 Hz), 8.44–8.47 (2H,m).

EXAMPLE 13

Ethyl 3-{3-[2-(3-methylbutanoylamino)ethyl]-5-(3-pyridylmethyl)phenyl}propanoate From preparation 47 and 3-methylbutanoyl chloride; Rf 0.30 (SS 1); δ (CDCl$_3$): 0.90(6H,d,J=.6.4 Hz), 1.21(3H,t,J= 7.1 Hz), 1.95(2H,d,J=7.0 Hz), 2.05(1H,m), 2.57(2H,t,J=7.7 Hz), 2.74(2H,t,J=6.9 Hz), 2.88(2H,t,J=7.7 Hz), 3.47(2H,m), 3.91(2H,s), 4.09(2H,q,J=7.1 Hz), 5.40(1H,br), 6.84(1H,s), 6.88(1H,s), 6.90(1H,s), 7.18–7.22(1H,m), 7.43–7.47 (1H, m), 8.44–8.47(2H,m).

EXAMPLE 14

Ethyl 3-[3-(2-phenylsulphonylamino)ethyl-5-(4-pyridylmethyl)phenyl]propanoate

From preparation 48 and phenylsulphonyl chloride; RF 0.60 (SS 1); δ (CDCl$_3$): 1.11(3H,t), 2.56(2H,t), 2.71(2H,t), 3.19–3.22(2H,m), 3.88(2H,s), 4.10(2H,q), 4.46(1H,t), 6.73(1H,s), 6.79(1H,s), 6.87(1H,s), 7.07(2H,d), 7.48–7.59(3H,m), 7.81(2H,d), 8.49(2H,d).

EXAMPLE 15

Ethyl 3-{3-[2-(4-chlorophenylsulphonylamino)ethyl]-5-(4-pyridylmethyl)phenyl}propanoate From preparation 48 and 4-chlorophenylsulphonyl chloride; Rf 0.60 (SS 1); δ (CDCl$_3$): 1.11(3H,t), 2.56(2H,t), 2.72(2H,t), 3.18–3.23(2H,m), 3.90(2H,s), 4.09(2H,q), 4.71(1H,t), 6.73(1H,s), 6.82(1H,s), 6.89(1H,s), 7.11(2H,d), 7.46(2H,d), 7.73(2H,d), 8.49(2H,d).

EXAMPLE 16

Ethyl 3-[3-(2-dimethylsulphamoylamino)ethyl-5-(4-pyridylmethyl)phenyl]propanoate From preparation 48 and dimethylsulphamoyl chloride; Rf 0.40 (SS 1); δ (CDCl$_3$): 1.12(3H,t), 2.59(2H,t), 2.75(3H, s), 2.80(2H,t), 2.90(2H,t), 3.26–3.32(2H,m), 3.91(2H,s), 4.10(2H,q), 6.85(1H,s), 6.90(1H,s), 6.93(1H,s), 7.09(2H,d), 8.50(2H,d).

EXAMPLE 17

Ethyl 3-{3-(4-pyridylmethyl)-5-[2-(1-pyrrolidinylsulphonylamino)ethyl]phenyl}propanoate From preparation 48 and 1-pyrrolidinylsulphonyl chloride; Rf 0.40 (SS 1); δ (CDCl$_3$): 1.11(3H,t), 2.84–2.90(4H, m), 2.59(2H,t), 2.81(2H,t), 2.90(2H,t), 3.10–3.20(6H,m), 3.91(2H,s), 4.10(2H,q), 6.87(1H,s), 6.90(1H,s), 6.93(1H,s), 7.10(2H,d), 8.49(2H,d).

EXAMPLE 18

Ethyl 3-[3-(2-phenylsulphonylamino)ethyl-5-(3-pyridyloxy)phenyl]propanoate

From Preparation 50 and phenylsulphonyl chloride; Rf 0.50 (SS 2). Found: C,63.24; H,5.59; N,6.19. $C_{24}H_{26}N_2O_5S$ requires C,63.41; H,5.77; N,6.16%.

EXAMPLE 19

Ethyl 3-{3-[2-(4-chlorophenylsulphonylamino)ethyl]-5-(3-pyridyloxy)phenyl}propanoate From Preparation 50 and 4-chlorophenylsulphonyl chloride; Rf 0.50 (SS 2). Found: C,58.69; H,5.15; N,5.66. $C_{24}H_{25}ClN_2O_5S$ requires C,58.95; H,5.15; N,5.73%.

EXAMPLE 20

Methyl 3-{3-[2-(4-chlorophenylsulphonylamino)ethyl]-5-(3-pyridylmethyl)phenyl}butanoate From Preparation 51 and 4-chlorophenylsulphonyl chloride; Rf 0.60 (SS 2); δ (CDCl$_3$): 1.22(3H,d,J=4.1 Hz), 2.50(2H,d,J=6.9 Hz), 2.70(2H,t,J=6.7 Hz), 3.15–3.19 (3H, m), 3.57(3H,s), 3.87(2H,s), 4.92–5.00(1H,m), 6.71(1H,s), 6.80(1H,s), 6.88(1H,s), 7.18–7.21(1H,m), 7.42–7.44(3H,m), 7.72(2H,d,J=8.2 Hz), 8.43(2H,m).

EXAMPLE 21

Methyl 2-{3-[2-(4-chlorophenylsulphonylamino)ethyl]-5-(3-pyridylmethyl)benzyl}propanoate From Preparation 52 and 4-chlorophenylsulphonyl chloride; Rf 0.60 (SS 2); δ (CDCl$_3$): 1.12(3H,d,J=6.6 Hz), 2.56–2.71(4H,m), 2.87–2.93(1H,m), 3.15–3.23(2H,m), 3.58(3H,s), 3.88(2H,s), 4.46–4.51(1H,m), 6.73(2H,s), 6.82(1H,s), 7.21–7.23(1H,m), 7.41–7.46(3H,m), 7.72(2H,d, J=8.4 Hz), 8.45(2H,m).

EXAMPLE 22 t-Butyl 3-{3-[2-(4-chlorophenylsulphonylamino)-1-propyl]-5-(3-pyridylmethyl)phenyl} propanoate From Preparation 53 and 4-chlorophenylsulphonyl chloride; Rf 0.70 (SS 2); δ (CDCl$_3$): 1.09(3H,d,J=6.5 Hz), 1.38(9H,s), 2.44(2H,t,J=7.7 Hz), 2.59(2H,d,J=6.6 Hz), 2.77(2H,t,J=7.7 Hz), 3.48(1H,m), 3.83(2H,s), 4.97(1H,d,J= 7.6 Hz), 6.65(1H,s), 6.70(1H,s), 6.84(1H,s), 7.17–7.20(1H, m), 7.32(2H,d,J=8.5 Hz), 7.42(1H,d,J=7.7 Hz), 7.59(2H,d, J=8.5 Hz), 8.42–8.44 (2H,m).

EXAMPLE 23

Ethyl 3-{3-[(α-hydroxy-α-methyl)-3-pyridylmethyl]-5-[(2-phenylsulphonylamino)ethyl] phenyl}propanoate From Preparation 54 and phenylsulphonyl chloride; Rf 0.50 (SS 1); δ (CDCl$_3$): 1.21(3H,t), 1.91(3H,s), 2.53(2H,t), 2.70(2H,t), 2.85(3H,t), 3.15–3.22(2H,m), 4.08(2H,q), 4.68–4.72(1H,m), 6.82(1H,s), 7.00(1H,s), 7.08(1H,s), 7.20–7.23(1H,m), 7.46–7.57(3H,m), 7.63–7.66 (1H,m), 7.78–7.81(2H,m), 8.43(1H,m), 8.56(1H,s).

EXAMPLE 24

Ethyl 3-{3-[2-(4-chlorophenylsulphonylamino)ethyl]-5-[(α-hydroxy-α-methyl)- 3-pyridylmethyl]phenyl}propanoate From Preparation 54 and 4-chlorophenylsulphonyl chloride; Rf 0.50 (SS 1); δ (CDCl$_3$): 1.26(3H,t), 1.96(3H,s), 2.57–2.62(3H,m), 2.77(2H,t), 2.92(2H,t), 3.21–3.26(2H,m), 4.12(2H,q), 4.10–4.15(1H,m), 6.87(1H,s), 7.04(1H,s), 7.13(1H,s), 7.25–7.30(1H,m), 7.49(2H,d), 7.72–7.77(3H,m), 8.50(1H,m), 8.63(1H,s).

EXAMPLE 25

Ethyl 3-{3-[3-(4-chlorophenylsulphonylamino)-1-propyl]-5-(3-pyridylmethyl)phenyl} propanoate From Preparation 55 and 4-chlorophenylsulphonyl chloride; Rf 0.50 (SS 2). Found: C,61.85; H,5.81; N,5.51. C$_{26}$H$_{29}$ClN$_2$O$_4$S requires C,62.32; H,5.83; N,5.59%

EXAMPLE 26

Ethyl 3-[3-(2-cyclohexylsulphonylamino)ethyl-5-(3-pyridylmethyl)phenyl]propanoate A solution of ethyl 3-[3-(2-aminoethyl)-5-(3-pyridylmethyl)phenyl]propanoate (Preparation 47; 0.60 g), cyclohexylsulphonyl chloride (0.526 g), triethylamine (0.194 g) and 4-dimethylaminopyridine (0.352 g) in dichloromethane (6 ml) was stirred at room temperature for 3 hours and then washed with water and dried (MgSO$_4$). Evaporation under vacuum of the solvent gave a gum which was chromatographed on silica gel. Elution with dichloromethane, followed by a dichloromethane:methanol (97:3) mixture gave the title compound as a gum (401 mg); Rf 0.70 (SS 2); δ (CDCl$_3$): 1.10–1.25(2H,m), 1.21(3H,t,J=7.1 Hz), 1.37–1.50(2H,m), 1.65–1.70(2H,m), 1.83–1.86(2H,m), 2.05–2.09(2H,m), 2.57(2H,t,J=7.7 Hz), 2.79(2H,t,J=6.9 Hz), 2.88 (2H,t,J=7.7 Hz), 3.30–3.37(2H,m), 3.91(2H,s), 3.99–4.02 (1H,m), 4.10(2H,q,J=7.1 Hz), 6.86(1H,s), 6.89(1H,s), 6.91(1H,s), 7.21–7.23(1H,m), 7.44(1H,d,J=7.9 Hz), 8.45–8.47 (2H,m).

The following five compounds were obtained from their respective amine precursors, using the appropriate sulphonyl chloride or sulphamoyl chloride, by procedures similar to that described in Example 26.

EXAMPLE 27

Ethyl 3-[3-(2-neopentylsulphonylamino)ethyl-5-(3-pyridylmethyl)phenyl]propanoate From Preparation 47 and neopentylsulphonyl chloride; Rf 0.75 (SS 2); δ (CDCl$_3$): 1.11(9H,s), 1.21(3H,t,J=7.1 Hz), 2.57(2H,t,J=7.7 Hz), 2.77–2.91 (6H,m), 3.33(2H,m), 3.92(2H,s), 4.06–4.18(3H,m), 6.86(1H,s), 6.90(1H,s), 6.91(1H,s), 7.18–7.25(1H,m), 7.45(1H,m), 8.45–8.47(2H,m).

EXAMPLE 28

Ethyl 3-[3-(2-diethylsulphamoylamino)ethyl-5-(3-pyridylmethyl)phenyl]propanoate

From Preparation 47 and diethylsulphamoyl chloride; Rf 0.75 (SS 3); δ (CDCl$_3$): 1.10(6H,t,J=7.2 Hz), 1.19(3H,t,J=7.1 Hz), 2.55(2H,t,J=7.8 Hz), 2.76(3H,t,J=7.0 Hz), 2.86(2H,t,J=7.8 Hz), 3.14–3.27 (6H,m), 3.89(2H,s), 4.07(2H,q,J=7.1 Hz), 4.39–4.42 (1H,m), 6.84(1H,s), 6.87(1H,s), 6.88(1H,s), 7.16–7.21 (1H,m), 7.44(1H,d,J=7.9 Hz), 8.41–8.45(2H,m).

EXAMPLE 29

Ethyl 3-{3-(3-pyridylmethyl)-5-[2-(1-pyrrolidinylsulphonylamino)ethyl]phenyl}propanoate From Preparation 47 and 1-pyrrolidinylsulphonyl chloride; δ (CDCl$_3$): 1.21(3H,m), 1.84–1.88(4H,m), 2.57(2H,t,J=7.7 Hz), 2.78(2H,t,J=6.8 Hz), 2.88(2H,t,J=7.7 Hz), 3.19–3.30(6H,m), 3.91(2H,s), 4.06–4.13(3H,m), 6.85(1H,s), 6.90(2H,s), 7.20–7.23(1H,m), 7.44–7.47 (1H,m), 8.45–8.48(2H,m).

EXAMPLE 30

Ethyl 3-[3-(2-piperidinosulphonylamino)ethyl-5-(3-pyridylmethyl)phenyl]propanoate From Preparation 47 and piperidinosulphonyl chloride; Rf 0.70 (SS 2); δ (CDCl$_3$): 1.21(3H,t,J=7.1 Hz), 1.50–1.70(6H,m), 2.57(2H,t,J=7.7 Hz), 2.78(2H,t,J=6.8 Hz), 2.88(2H,t,J=7.7 Hz), 3.05–3.10 (4H,m), 3.22–3.29(2H,m), 3.92(2H,s), 3.97–4.01 (1H,m), 4.10(2H,q,J=7.1 Hz), 6.85(1H,s), 6.90(2H,s), 7.20–7.22(1H,m), 7.45(1H,d,J=7.7 Hz), 8.45–8.48 (1H,m).

EXAMPLE 31

Ethyl 3-{3-[2-(2-isoindolinylsulphonylamino)ethyl]-5-(3-pyridylmethyl)phenyl}propanoate From Preparation 47 and 2-isoindolinylsulphonyl chloride; Rf 0.70 (SS 2); δ (CDCl$_3$): 1.21(3H,t,J=7.1 Hz), 2.54(2H,t,J=7.7 Hz), 2.75–2.87(4H,m), 3.30–3.35 (2H,m), 3.87(2H,s), 4.09(2H,q,J=7.1 Hz), 4.15(1H,t), 4.57(4H,s), 6.82(1H,s), 6.87(2H,s), 7.17–7.30 (5H,m), 7.41(1H,m), 8.46(2H,m).

EXAMPLE 32

Ethyl 3-{3-(1-imidazolylmethyl)-5-[(2-phenylsulphonylamino)ethyl]phenyl}propanoate A solution of phenylsulphonyl chloride (0.258 g) in dichloromethane (1 ml) was added to a stirred solution of ethyl 3-[3-(2-aminoethyl)-5-(1-imidazolylmethyl)phenyl]propanoate (Preparation 49; 0.40 g) and 4-dimethylaminopyridine (0.179 g) in dichloromethane (4 ml) at room temperature. The solution was stirred for 1 hour, washed with water and dried (MgSO$_4$). The solvent was evaporated under vacuum and the residue was chromatographed on silica gel. Elution with a dichloromethane:methanol (50:1) mixture gave the title compound as a gum (0.375 g); Rf 0.45 (SS 2). Found: C,61.99; H,6.07; N,9.39. C$_{23}$H$_{27}$N$_3$O$_4$S requires C,62.56; H,6.16; N,9.52%

The following two compounds were obtained from the same amine precursor, using the appropriate sulphonyl chloride, by procedures similar to that described in Example 32.

EXAMPLE 33

Ethyl 3-{3-[2-(4-fluorophenylsulphonylamino)ethyl]-5-(1-imidazolylmethyl)phenyl}propanoate From Preparation 49 and 4-fluorophenylsulphonyl chloride; Rf 0.50 (SS 2). Found: C,60.03; H,5.72; N,9.06. C$_{23}$H$_{26}$FN$_3$O$_4$S requires C,60.11; H,5.70; N,9.15%.

EXAMPLE 34

Ethyl 3-{3-[2-(4-chlorophenylsulphonylamino)ethyl]-5-(1-imidazolylmethyl)phenyl}propanoate From Preparation 49 and 4-chlorophenylsulphonyl chloride; Rf 0.50 (SS 2). Found: C,58.15; H,5.48; N,8.63. C$_{23}$H$_{26}$ClN$_3$O$_4$S requires C,58.03; H,5.51; N,8.83%.

EXAMPLE 35

Ethyl 3-{3-[2-[1-(2,5-dihydropyrrolyl)sulphonylamino]ethyl]-5-(3-pyridylmethyl)phenyl}propanoate A solution of ethyl 3-[3-(2-aminoethyl)-5-(3-pyridylmethyl)phenyl]propanoate (Preparation 47; 0.40 g) and 4-dimethylaminopyridine (0.156 g) in dichloromethane (4 ml) was added dropwise over 25 minutes to a stirred solution of sulphuryl chloride (0.207 g) in dichloromethane (1 ml) at −75° C. The mixture was stirred at −75° C. for 15 minutes, at room temperature for a further 1 hour, then cooled again to −75° C. and 2,5-dihydropyrrole (0.265 g) added. This mixture was stirred at room temperature for 3 hours, washed with water and dried (MgSO$_4$). The solvent was evaporated under vacuum and the residue chromatographed on silica gel using a dichloromethane:methanol (99:1) mixture as eluent. The product-containing fractions were combined and evaporated under vacuum to give the title compound as an oil (0.171 g); Rf 0.60 (SS 2); δ (CDCl$_3$): 1.21(3H,t,J=7.1 Hz), 2.57(2H,t,J=7.8 Hz), 2.79(2H,t,J=6.85 Hz), 2.88(2H,t,J=7.8 Hz), 3.30(2H,m), 3.92(2H,s), 4.07(4H,s), 4.10(2H,q,J=7.1 Hz), 5.73(2H,s), 6.85(1H,s), 6.90(2H,s), 7.19–7.23(1H,m), 7.45(1H,d,J=7.8 Hz), 8.46–8.48(2H,m).

The following three compounds were obtained from the same amine precursor, via the derived sulphamoyl chloride generated in situ and the appropriate amine, by procedures similar to that described in Example 35.

EXAMPLE 36

Ethyl 3-{3-[2-[1-(1,2,3,6-tetrahydropyridyl)sulphonylamino]ethyl]-5-(3-pyridylmethyl)phenyl}propanoate From Preparation 47 and 1,2,3,6-tetrahydropyridine; Rf 0.60 (SS 2). Found: C,66.08; H,6.55; N,8.05. C$_{24}$H$_{31}$N$_3$O$_4$S requires C,66.45; H,6.75; N,8.16%.

EXAMPLE 37

Ethyl 3-{3-[2-[1-(4-methyl-1,2,3,6-tetrahydropyridyl)sulphonylamino]ethyl]-5-(3-pyridylmethyl)phenyl}propanoate From Preparation 47 and 4-methyl-1,2,3,6-tetrahydropyridine; Rf 0.75 (SS 2); δ (CDCl$_3$): 1.21(3H,t,J=7.1 Hz), 1.70(3H,s), 2.05–2.12(2H,m), 2.57(2H,t,J=7.8 Hz), 2.77(2H,t,J=6.9 Hz), 2.88(2H,t,J=7.8 Hz), 3.23–3.29(4H,m), 3.60(2H,s), 3.91(2H,s), 4.10(2H,q,J=7.1 Hz), 5.34(1H,s), 6.84(2H,s), 7.20–7.26(1H,m), 7.45(1H,d,J=7.8 Hz), 8.45–8.50 (2H,m).

EXAMPLE 38

Ethyl 3-{3-[2-(4-chlorophenylsulphamoylamino)ethyl]-5-(3-pyridylmethyl)phenyl}propanoate From Preparation 47 and 4-chloroaniline; Rf 0.30 (SS 1). Found: C,59.72; H,5.68; N,8.41. C$_{25}$H$_{28}$ClN$_3$O$_4$S requires C,59.81; H,5.62; N,8.37%.

EXAMPLE 39

Ethyl 3-{3-(2-phenylsulphonylamino)ethyl-5-[1-(3-pyridyl)ethenyl]phenyl}propanoate A solution of ethyl 3-{3-[(α-hydroxy-α-methyl)-3-pyridylmethyl]-5-[(2-phenylsulphonylamino)ethyl]phenyl}propanoate (Example 23; 0.13 g) in trifluoroacetic acid (5 ml) was heated at 50° C. for 4 hours and then evaporated under vacuum. The residue was partitioned between ethyl acetate and aqueous sodium bicarbonate solution, then the organic phase separated, washed with brine and dried (MgSO$_4$). Evaporation under vacuum of the solvent gave the title compound as an oil (0.12 g); Rf 0.60 (SS 1); δ (CDCl$_3$): 1.21(3H,t), 2.56(2H,t), 2.72(2H,t), 2.89(2H,t), 3.19–3.24 (2H,m), 4.11(2H,q), 5.49(1H,s), 5.51(1H,s), 6.84(1H,s), 6.91(1H,s), 7.01(1H,s), 7.24–7.30(1H,m), 7.46–7.58(4H,m), 7.80–7.82(2H,m), 8.55(2H,m).

The following compound was obtained from its tertiary alcohol precursor by a procedure similar to that described in Example 39.

EXAMPLE 40

Ethyl 3-{3-[2-(4-chlorophenylsulphonylamino)ethyl]-5-[1-(3-pyridyl)ethenyl]phenyl} propanoate From Example 24; Rf 0.65 (SS 1); δ (CDCl$_3$): 1.21(3H,t), 2.57(2H,t), 2.75(2H,t), 2.89(2H,t); 3.19–3.25 (2H,m), 4.10(2H,q), 4.25–4.30(1H,m), 5.49(1H,s), 5.50(1H,s), 6.83(1H,s), 6.92(1H,s), 7.01(1H,s), 7.23–7.30 (1H,m), 7.44(2H,d), 7.53–7.58(1H,m), 7.72(2H,d), 8.55(2H,m).

EXAMPLE 41

Ethyl 3-{3-(2-phenylsulphonylamino)ethyl-5-[1-(3-pyridyl)ethyl]phenyl}propanoate A solution of ethyl 3-{3-(2-phenylsulphonylamino)ethyl-5-[1-(3-pyridyl)ethenyl]phenyl}propanoate (Example 39; 0.13 g) in ethanol (5 ml) was hydrogenated at 20° C. and 50 p.s.i. (3.45 bar) for 5 hours in the presence of 10% palladium on charcoal catalyst (30 mg). The mixture was then filtered, the residue washed with ethanol, and the combined filtrate and washings evaporated under vacuum to give the title compound as a gum (0.12 g); Rf 0.65 (SS 1); δ (CDCl$_3$): 1.21(3H,t), 1.60(3H,d), 2.53(2H,t), 2.69(2H,t), 2.85(2H,t), 3.18–3.23 (2H,m), 3.72(1H,q), 4.08(2H,q), 4.32–4.38(1H,m), 6.76(2H,s), 6.90(1H,s), 7.18–7.22(1H,m), 7.42–7.60 (4H,m), 7.78–7.80(2H,m), 8.42–8.44(2H,m).

The following compound was obtained from its alkene precursor by a procedure similar to that described in Example 41.

EXAMPLE 42

Ethyl 3-{3-[2-(4-chlorophenylsulphonylamino)ethyl]-5-[1-(3-pyridyl)ethyl]phenyl} propanoate From Example 40; Rf 0.70 (SS 1); δ (CDCl$_3$): 1.21(3H,t), 1.61(3H,d), 2.56(2H,t), 2.70(2H,t), 2.85(2H,t), 3.15–3.22(2H,m), 3.70(1H,q), 4.08(2H,q), 4.51–4.56(1H,m), 6.77(2H,s), 6.90(1H,s), 7.22–7.26 (1H,m), 7.45(2H,d), 7.47–7.52(1H,m), 7.73(2H,d), 8.43–8.50(2H,m).

EXAMPLE 43

Ethyl 3-[3-(2-phenylsulphonylethyl)-5-(3-pyridylmethyl)phenyl]propanoate

A mixture of ethyl 3-(2-phenylsulphonylethenyl)-5-(3-pyridylmethyl)cinnamate (Preparation 20; 0.485 g) and 4-methylphenylsulphonyl hydrazine (2.08 g) in toluene (25 ml) was heated under reflux for 3 hours and then evaporated under vacuum. The residue was chromatographed on silica gel using an ethyl acetate in hexane elution gradient (50 to 100% ethyl acetate) initially followed by an ethyl acetate:diethylamine (95:5) mixture as eluent. The product fractions were combined and evaporated under vacuum to give the title compound as a gum (0.384 g); Rf 0.50 (SS 4); δ (CDCl$_3$): 1.23(3H,t), 2.57(2H,t), 2.86(2H,t), 2.99(2H,m), 3.33(2H,m), 3.91(2H,s), 4.13(2H,q), 6.82(1H,s), 6.87(1H,s), 6.91(1H,s), 7.22–7.25(1H,m), 7.43–7.47 (1H,m), 7.57–7.72(3H,m), 7.94–7.98(2H,m), 8.48–8.51(2H,m).

The following compound was obtained from its alkene precursor by a procedure similar to that described in Example 43.

EXAMPLE 44

Ethyl 3-[3-(3-phenylsulphonyl-1-propyl]-5-(3-pyridylmethyl)phenyl]propanoate

From Preparation 21; Rf 0.50 (SS 4); δ (CDCl$_3$): 1.21(3H, t), 1.97–2.03(2H,m), 2.53–2.65(4H,m), 2.87(2H,t), 3.04(2H, t), 3.90(2H,s), 4.10(2H,q), 6.77(1H,s), 6.82(1H,s), 6.87(1H, s), 7.18–7.22(1H,m), 7.41–7.45(1H,m), 7.54–7.68(3H,m), 8.88(2H,d), 8.47(2H,m).

EXAMPLE 45

3-[3-(2-phenylsulphonylamino)ethyl-5-(3-pyridylmethyl)phenyl]propanoic acid

A solution of ethyl 3-[3-(2-phenylsulphonylamino)ethyl-5-( 3-pyridylmethyl)phenyl]propanoate (Example 1; 1.90 g) in a mixture of 2N aqueous sodium hydroxide solution (6.0 ml) and methanol (10 ml) was heated under reflux for 45 minutes and then evaporated under vacuum. The residue was dissolved in water and the resulting solution was washed with ethyl acetate and then acidified to pH 4–5 with glacial acetic acid. The resulting gum solidified on scratching and this solid was collected, washed with water and dried, to afford the title compound (1.09 g), m.p. 137°–139° C. Found: C,65.25; H,5.87; N,6.70. C$_{23}$H$_{24}$N$_2$O$_4$S requires: C,65.07; H,5.70; N,6.60%

The following forty two compounds were obtained from their respective precursor esters by procedures similar to that described in Example 45.

EXAMPLE 46

3-{3-[2-(4-Methylphenylsulphonylamino)ethyl]-5-(3-pyridylmethyl)phenyl}propanoic acid From Example 2; m.p. 130°–132° C. Found: 65.54; H,6.01; N,6.16. C$_{24}$H$_{26}$N$_2$O$_4$S requires C,65.73; H,5.98; N,6.39%.

EXAMPLE 47

3-{3-[2-(4-Fluorophenylsulphonylamino)ethyl]-5-(3-pyridylmethyl)phenyl}propanoic acid From Example 3; m.p. 132°–134° C. Found: C,62.38; H,5.26; N,6.24. C$_{23}$H$_{23}$FN$_2$O$_4$S requires C,62.42; H,5.24; N,6.33%.

EXAMPLE 48

3-{3-[2-(4-Chlorophenylsulphonylamino)ethyl]-5-(3-pyridylmethyl)phenyl}propanoic acid From Example 4; m.p. 150°–152° C. Found: C,60.05; H,5.08; N,6.07. C$_{23}$H$_{23}$ClN$_2$O$_4$S requires C,60.19; H,5.05; N,6.10%.

EXAMPLE 49

3-{3-[2-(4-Bromophenylsulphonylamino)ethyl]-5-(3-pyridylmethyl)phenyl}propanoic acid From Example 5; m.p. 136°–138° C. Found: C,54.85; H,4.41; N,5.52. C$_{23}$H$_{23}$BrN$_2$O$_4$S requires C,54.87; H,4.61; N,5.57%.

EXAMPLE 50

3-{3-[2-Furylsulphonylamino)ethyl]-5-(3-pyridylmethyl)phenyl}propanoic acid

From Example 6; Rf 0.20 (SS 5). Found: C,60.74; H,5.41; N,6.64. C$_{21}$H$_{22}$N$_2$O$_5$S requires C,60.85; H,5.35; N,6.76%.

EXAMPLE 51

3-[3-(2-Methylsulphonylamino)ethyl-5-(3-pyridylmethyl)phenyl]propanoic acid

From Example 7; m.p. 118°–120° C. Found: C,60.05; H,6.05; N,7.67. C$_{18}$H$_{22}$N$_2$O$_4$S requires C,59.66; H,6.12; N,7.73%.

EXAMPLE 52

3-{3-[2-(1-Propylsulphonylamino)ethyl]-5-(3-pyridylmethyl)phenyl}propanoic acid

From Example 8; m.p. 102°–103° C. Found: C,61.65; H,6.71; N,7.12. C$_{20}$H$_{26}$N$_2$O$_4$S requires C,61.51; H,6.71; N,7.17%.

EXAMPLE 53

3-{3-[2-(2-Propylsulphonylamino)ethyl]-5-(3-pyridylmethyl)phenyl}propanoic acid

From Example 9; m.p. 81°–83° C.; δ (DMSOd$_6$): 1.07 (6H,d,J=6.75 Hz), 2.46(2H,m), 2.61–2.73(4H,m), 2.97–3.12 (3H,m), 3.85(2H,s), 6.90(2H,s), 6.94(1H,s), 7.01–7.05 (1H, m), 7.23–7.27(1H,m), 7.57(1H,d,J=7.85 Hz), 8.35(1H,d,J=4 Hz), 8.46(1H,s).

EXAMPLE 54

3-[3-(2-Dimethylsulphamoylamino)ethyl-5-(3-pyridylmethyl)phenyl]propanoic acid

From Example 11; m.p. 76°–78° C. Found: C,57.95; H,6.13; N,10.40. C$_{19}$H$_{25}$N$_3$O$_4$S requires C,58.29; H,6.44; N,10.73%.

EXAMPLE 55

3-[3-(2-Benzoylamino)ethyl-5-(3-pyridylmethyl)phenyl] propanoic acid

From Example 12; m.p. 115°–117° C. Found: C,73.79; H,6.02; N,6.92. C$_{24}$H$_{24}$N$_2$O$_3$ requires C,74.20; H,6.23; N,7.21%.

EXAMPLE 56

3-{3-[2-(3-Methylbutanoylamino)ethyl]-5-(3-pyridylmethyl)phenyl}propanoic acid

From Example 13; m.p. 131°–132° C. Found: C,71.63; H,7.48; N,7.43. C$_{22}$H$_{28}$N$_2$O$_3$ requires C,71.7 1; H,7.66; N,7.60%.

EXAMPLE 57

3-[3-(2-Phenylsulphonylamino)ethyl-5-(4-pyridylmethyl)phenyl}propanoic acid

From Example 14; m.p. 129°–131° C. Found: C,64.89; H,5.68; N,6.55. C$_{23}$H$_{24}$N$_2$O$_4$S requires C,65.07; H,5.70; N,6.60%.

EXAMPLE 58

3-{3-[2-(4-Chlorophenylsulphonylamino)ethyl]-5-(4-pyridylmethyl)phenyl}propanoic acid From Example 15; m.p. 159°–160° C. Found: C,59.99; H,5.05; N,6.07. C$_{23}$H$_{23}$ClN$_2$O$_4$S requires C,60.19; H,5.05; N,6.10%.

EXAMPLE 59

3-[3-(2-Dimethylsulphamoylamino)ethyl-5-(4-pyridylmethyl)phenyl]propanoic acid

From Example 16; Rf 0.30 (SS 6); δ (DMSOd$_6$): ca 2.45(2H+DMSOd$_5$), 2.52(6H,s), 2.64(2H,t), 2.73(2H,t), 3.03(2H,t), 3.96(2H,s), 6.89(2H,s), 6.91(1H,s), 7.17(2H,d), 8.39(2H,d).

EXAMPLE 60

3-{3-(4-Pyridylmethyl)-5-[2-(1-pyrrolidinylsulphonylamino)ethyl]phenyl}propanoic acid From Example 17; m.p. 118°–121° C. Found: C,59.76; H,6.43; N,9.81. $C_{21}H_{27}N_3O_4S$ requires C,59.76; H,6.57; N,9.96%.

EXAMPLE 61

3-[3-(2-Phenylsulphonylamino)ethyl-5-(3-pyridyloxy)phenyl]propanoic acid

From Example 18; m.p. 99°–101° C. Found: C,62.12; H,5.25; N,6.54. $C_{22}H_{22}N_2O_5S$ requires C,61.95; H,5.20; N,6.57%.

EXAMPLE 62

3-{3-[2-(4-Chlorophenylsulphonylamino)ethyl]-5-(3-pyridyloxy)phenyl}propanoic acid From Example 19; m.p. 112°–115° C. Found: C,57.32; H,4.60; N,6.04. $C_{22}H_{21}ClN_2O_5S$ requires C,57.32; H,4.59; N,6.08%

EXAMPLE 63

3-{3-[2-(4-Chlorophenylsulphonylamino)ethyl]-5-(3-pyridylmethyl)phenyl}butanoic acid From Example 20; m.p. 114°–116° C. Found: C,61.30; H,5.15; N,5.96. $C_{24}H_{25}ClN_2O_4S$ requires C,60.94; H,5.33; N,5.92%.

EXAMPLE 64

2-{3-[2-(4-Chlorophenylsulphonylamino)ethyl]-5-(3-pyridylmethyl)benzyl}propanoic acid From Example 21; Rf 0.55 (SS 7). Found: C,60.94; H,5.46; N,5.88. $C_{24}H_{25}ClN_2O_4S$ requires C,60.94; H,5.33; N,5.92%.

EXAMPLE 65

3-{3-[2-(4-Chlorophenylsulphonylamino)-1-propyl]-5-(3-pyridylmethyl)phenyl}propanoic acid From Example 22; m.p. 74°–76° C. Found: C,60.79; H,5.52; N,5.64. $C_{24}H_{25}ClN_2O_4S$ requires C,60.94; H,5.33; N,5.92%.

EXAMPLE 66

3-{3-[(α-Hydroxy-α-methyl)-3-pyridylmethyl]-5-[(2-phenylsulphonylamino)ethyl]phenyl} propanoic acid From Example 23; Rf 0.25 (SS 1). Found: C,58.31; H,5.65; N,5.99. $C_{24}H_{26}N_2O_5S$; $2H_2O$ requires C,58.76; H,6.16; N,5.71%.

EXAMPLE 67

3-{3-[2-(4-Chlorophenylsulphonylamino)ethyl]-5-[(α-hydroxy-α-methyl)-3-pyridylmethyl] phenyl}propanoic acid From Example 24; Rf 0.50 (SS 6). Found: C,58.34; H,5.09; N,5.50. $C_{24}H_{25}ClN_2O_5S$; 0.25 $H_2O$ requires C,58.41; H,5.21; N,5.67%.

EXAMPLE 68

3-{3-[3-(4-Chlorophenylsulphonylamino)-1-propyl]-5-(3-pyridylmethyl)phenyl}propanoic acid From Example 25; m.p. 112°–115° C. Found: C,60.82; H,5.53; N,5.84. $C_{24}H_{25}ClN_2O_4S$ requires C,60.94; M,5.33; N,5.92%.

EXAMPLE 69

3-[3-(2-Cyclohexylsulphonylamino)ethyl-5-(3-pyridylmethyl)phenyl]propanoic acid

From Example 26; Rf 0.50 (SS 7); δ (CDCl$_3$): 1.07–1.24 (2H,m), 1.33–1.44(2H,m), 1.63–1.66(1H,m), 1.78–1.82 (2H,m), 1.97–2.05(2H,m), 2.53(2H,m), 2.73–2.85 (4H,m), 3.30(2H,m), 3.89(2H,s), 4.81(1H,s), 6.82(1H,s), 6.88(1H,s), 6.94(1H,s), 7.19–7.23(1H,m), 7.49(1H,d,J=7.65 Hz), 8.39–8.42(2H,m).

EXAMPLE 70

3-[3-(2-Neopentylsulphonylamino)ethyl-5-(3-pyridylmethyl)phenyl]propanoic acid

From Example 27; m.p. 117°–119° C. Found: C,62.75; H,7.15; N,6.56. $C_{22}H_{30}N_2O_4S$ requires C,63.13; H,7.23; N,6.69%.

EXAMPLE 71

3-[3-(2-Diethylsulphonylamino)ethyl-5-(3-pyridylmethyl)phenyl]propanoic acid

From Example 28; m.p. 104°–106° C. Found: C,60.50; H,6.90; N,9.92. $C_{21}H_{29}N_3O_4S$ requires C,60.12; H,6.97; N,10.01%.

EXAMPLE 72

3-{3-(3-Pyridylmethyl)-5-[2-(1-pyrrolidinylsulphonylamino)ethyl]phenyl}propanoic acid From Example 29; m.p. 86°–88° C. Found: C,60.22; H,6.35; N,9.85. $C_{21}H_{27}N_3O_4S$ requires C,60.41; H,6.51; N,10.07%.

EXAMPLE 73

3-[3-(2-Piperidinosulphonylamino)ethyl-5-(3-pyridylmethyl)phenyl]propanoic acid

From Example 30; Rf 0.45 (SS 7). Found: C,60.79; H,6.83; N,9.54. $C_{22}H_{29}N_3O_4S$ requires C,61.22; H,6.77; N,9.74%.

EXAMPLE 74

3-{3-[2-(2-Isoindolinylsulphonylamino)ethyl]-5-(3-pyridylmethyl)phenyl}propanoic acid From Example 31; m.p. 137°–139° C. Found: C,63.78; H,5.60; N,8.62. $C_{25}H_{27}N_3O_4S$ requires C,64.49; H,5.85; N,9.03%.

EXAMPLE 75

3-{3-(1-Imidazolylmethyl)-5-[(2-phenylsulphonylamino)ethyl]phenyl}propanoic acid From Example 32; m.p. 123°–125° C. Found: C,61.12; H,5.97; N,10.02. $C_{21}H_{23}N_3O_4S$ requires C,61.00; H,5.61; N,10.16%.

EXAMPLE 76

3-{3-[2-(4-Fluorophenylsulphonylamino)ethyl]-5-(1-imidazolylmethyl)phenyl}propanoic acid From Example 33; m.p. 146°–147° C. Found: C,58.25; H,4.97; N,9.51. $C_{21}H_{22}FN_3O_4S$ requires C,58.45; H,5.14; N,9.74%.

EXAMPLE 77

3-{3-[2-(4-Chlorophenylsulphonylamino)ethyl]-5-(1-imidazolylmethyl)phenyl}propanoic acid From Example 34; m.p. 185°–187° C. Found: C,56.03; H,4.89; N,9.01. $C_{21}H_{22}ClN_3O_4S$ requires C,56.30; H,4.95; N,9.35%.

EXAMPLE 78

3-{3-[2-[1-(2,5-Dihydropyrrolyl)sulphonylamino]ethyl]-5-(3-pyridylmethyl)phenyl}propanoic acid From Example 35; Rf 0.20 (SS 2); δ (CDCl$_3$): 2.61(2H, t,J=7.3 Hz), 2.78(2H,t,J=6.6 Hz),2.91(2H,t,J=7.3 Hz), 3.29(2H,m), 3.93(2H,s), 4.05(4H,s), 4.48 (1H,s), 5.71(2H, s), 6.84(1H,s), 6.92(1H,s), 6.94(1H,s), 7.23–7.27(1H,m), 7.54(1H,d,J=7.8 Hz), 8.42(1H,d,J=4.3 Hz), 8.46(1H,s).

EXAMPLE 79

3-{3-[2-[1-(1,2,3,6-Tetrahydropyridyl)sulphonylamino] ethyl]-5-( 3-pyridylmethyl)phenyl}propanoic acid From Example 36; Rf 0.50 (SS 7). Accurate mass: found $(MH)^+$ 430.17914; $C_{22}H_{27}N_3O_4S$ requires $(MH)^+$ 430.180054.

EXAMPLE 80

3-{3-[2-[1-(4-Methyl-1,2,3,6-tetrahydropyridyl)sulphonylamino]ethyl]-5-( 3-pyridylmethyl)phenyl}propanoic acid From Example 37; Rf 0.70 (SS 7); δ (CDCl$_3$): 1.68(3H,s), 2.06(2H,m), 2.60(2H,t,J=7.35 Hz), 2.76(2H,t,J=6.6 Hz), 2.90 (2H,t,J=7.35 Hz), 3.22–3.26 (4H,m), 3.58(2H,s), 3.92(2H,s), 4.42(1H,s), 5.32(1H,s), 6.83(1H,s), 6.91(1H,s), 6.93(1H,s), 7.22–7.26 (1H,m), 7.52(1H,d,J=7.8 Hz), 8.41(1H,d,J=4.3 Hz), 8.45(1H,s).

EXAMPLE 81

3-{3-[2-(4-Chlorophenylsulphamoylamino)ethyl]-5-(3-pyridylmethyl)phenyl}propanoic acid From Example 38; m.p. 133°–136° C. Found: C,58.32; H,5.21; N,8.89. $C_{23}H_{24}ClN_3O_4S$ requires C,58.28; H,5.10; N,8.87%.

EXAMPLE 82

3-{3-(2-Phenylsulphonylamino)ethyl-5-[1-(3-pyridyl)ethenyl]phenyl}propanoic acid From Example 39; Rf 0.60 (SS 6); δ (DMSOd$_6$): ca 2.45(2H+DMSOd$_5$), 2.59(2H,t), 2.71(2H,t), 2.88–2.94 (2H, m), 5.50(1H,s), 5.52(1H,s), 6.83(1H,s), 6.98(2H,s), 7.32–7.38(1H,m), 7.48–7.72(6H,m), 8.47–8.51 (2H,m), 12.08(1H,s).

EXAMPLE 83

3-{3-[2-(4-Chlorophenylsulphonylamino)ethyl]-5-[1-(3-pyridyl)ethenyl]phenyl} propanoic acid From Example 40; Rf 0.50 (SS 6). Found: C,61.04; H,4.50; N,5.79. $C_{24}H_{23}ClN_2O_4S$ requires C,61.20; H,4.90; N,5.95%.

EXAMPLE 84

3-{3-(2-Phenylsulphonylamino)ethyl-5-[1-(3-pyridyl)ethyl] phenyl}propanoic acid

From Example 41; Rf 0.25 (SS 1); δ (DMSOd$_6$): 1.51(3H, d), 2.42(2H,t), 2.55(2H,t), 2.68(2H,t), 2.85–2.92 (2H,m), 4.06(1H,q), 6.77(1H,s), 6.84(1H,s), 6.95(1H,s), 7.21–7.25(1H,m), 7.48–7.72(6H,m), 8.32(1H,m), 8.44(1H, m).

EXAMPLE 85

3-{3-[2-(4-Chlorophenylsulphonylamino)ethyl]-5-[1-(3-pyridyl)ethyl]phenyl}propanoic acid From Example 42; Rf 0.50 (SS 6). Found: C,60.38; H,5.57; N,5.45. $C_{24}H_{25}ClN_2O_4S$; 0.33 $H_2O$ requires C,60.18; H,5.40; N,5.85%.

EXAMPLE 86

3-[3-(2-Phenylsulphonylethyl)-5-(3-pyridylmethyl)phenyl] propanoic acid

From Example 43; m.p. 156°–158° C. Found: C,67.29; H,5.84; N,3.48. $C_{23}H_{23}NO_4S$ requires C,67.46; H,5.66; N,3.42%.

EXAMPLE 87

3-[3-(3-Phenylsulphonyl-1-propyl)-5-(3-pyridylmethyl)phenyl]propanoic acid

From Example 44; m.p. 121°–123° C. Found: C,67.58; H,5.97; N,3.41. $C_{24}H_{25}NO_4S$ requires C,68.06; H,5.95; N,3.31%.

EXAMPLE 88

3-{3-(3-Pyridylmethyl)-5-[2-(2,2,2-trifluoroethylsulphonylamino)ethyl]phenyl}propanoic acid A stirred solution of ethyl 3-{3-(3-pyridylmethyl)- 5-[2-(2,2,2-trifluoroethylsulphonylamino)ethyl] phenyl}propanoate (Example 10; 400 mg) in 6N hydrochloric acid (4.0 ml) was heated at 100° C. for 4 hours. The cool solution was basified with aqueous ammonia solution (SG 0.880) and then re-acidified by the dropwise addition of glacial acetic acid. The mixture was extracted several times with ethyl acetate and the combined extracts were washed with water and dried (MgSO$_4$). Evaporation under vacuum of the solvent gave the title compound as a gum (265 mg); Rf 0.35 (SS 7). Found: C,53.26; H,4.78; N,6.31. $C_{19}H_{21}F_3N_2O_4S$ requires C,53.01; H,4.92; N,6.51%.

PREPARATION 1

3-(3,5-Dibromobenzoyl)pyridine

A 2.5M solution of n-butyllithium in hexane (40.0 ml) was added dropwise to a stirred mixture of 1,3,5-tribromobenzene (31.5 g) and dry ether (1000 ml) at −78° C. under an atmosphere of dry nitrogen. The resulting solution was stirred at −78° C. for 30 minutes and then a solution of 3-cyanopyridine (10.4 g) in dry ether (100 ml) was added dropwise. The mixture was stirred at −78° C. for 1 hour and then the temperature was allowed to reach 0° C. 2N Hydrochloric acid (200 ml) was added, with stirring, and the ether layer was decanted off and then extracted several times with 2N hydrochloric acid. The acidic extracts were combined and warmed on a steam bath for 20 minutes, then the solution was cooled and basified with aqueous potassium hydroxide solution. The resulting solid was filtered off, washed with water, dried and combined with the solid obtained by evaporation under vacuum of the ether solution. The crude product was chromatographed on silica gel using dichloromethane as eluent; the earlier fractions contained impurity and the later fractions were combined and evaporated under vacuum. The solid obtained from the latter fractions was crystallised from ethyl acetate-hexane to give the title compound (23.33 g), m.p. 124°–126° C. Found: C,42.50; H,2.23; N,4.21. $C_{12}H_7Br_2NO$ requires C,42.26; H,2.07; N,4.11%.

PREPARATION 2

4-(3,5-Dibromobenzoyl)pyridine

This isomer was obtained by a procedure similar to that described in Preparation 1, using 4-cyanopyridine as starting material; m.p. 89°–92° C.; δ ($CDCl_3$): 7.55(2H,d), 7.83(2H, s), 7.92(1H,s), 8.86(2H,d).

PREPARATION 3

3-(3,5-Dibromobenzyl)pyridine

A solution of 3-(3,5-dibromobenzoyl)pyridine (Preparation 1; 19.0 g) and hydrazine hydrate (13.9 ml) in ethylene glycol (140 ml) was heated under reflux for 45 minutes. The volatile material was distilled off until the internal temperature reached 180° C., and then the reaction mixture was cooled to 80° C. Potassium hydroxide (7.80 g) was added and the resulting solution was heated under reflux for 30 minutes, cooled and then poured into water. The mixture was extracted several times with ethyl acetate, and the combined extracts were washed with water and dried ($MgSO_4$). Evaporation under vacuum gave the title compound (16.38 g), m.p. 70°–72° C. (after crystallisation from ethyl acetate-hexane). Found: C,44.29; H,2.66; N,4.29. $C_{12}H_9Br_2N$ requires C,44.07; H,2.77; N,4.28%.

PREPARATION 4

4-(3,5-Dibromobenzyl)pyridine

This isomer was obtained by a procedure similar to that described in Preparation 3; m.p. 95°–97° C.; δ ($CDCl_3$): 3.90(2H,s), 7.08(2H,d), 7.23(2H,s), 7.54(1H,s), 8.53(2H,d).

PREPARATION 5

1,3-Dibromo-5-[(α-hydroxy-α-methyl)-3-pyridylmethyl]benzene

A 2.5M solution of n-butyllithium in hexane (20.0 ml) was added dropwise to a stirred mixture of 1,3,5-tribromobenzene (15.74 g) in dry ether (550 ml) at –78° C. under an atmosphere of dry nitrogen. The resulting mixture was stirred at this temperature for 30 minutes and then a solution of 3-acetylpyridine (6.06 g) in dry ether (50 ml) was added dropwise. This mixture was stirred at about –55° C. for 30 minutes and then allowed to warm to room temperature before being quenched with saturated brine. The organic phase was separated, washed with saturated brine and dried ($MgSO_4$). Evaporation under vacuum of the solvent gave a residue which was triturated with hexane to give the title compound (13.22 g), m.p. 152°–155° C.; δ ($CDCl_3$): 1.95(3H,s), 2.39(1H,s), 7.49(2H,s), 7.55(1H,s), 7.69–7.72 (1H,m), 8.50(1H,m), 8.66(1H,m).

PREPARATION 6

3-(3,5-Dibromophenoxy)pyridine

Sodium hydride (3.24 g of a 60% dispersion in mineral oil) was added portionwise to a stirred mixture of 3-hydroxypyridine (15.4 g), 1,3,5-tribromobenzene (76.4 g), cuprous oxide (11.6 g) and collidine (400 ml). When evolution of hydrogen had ceased, the mixture was heated at 200° for 8 hours and then cooled. The cool mixture was diluted with ethyl acetate and water, basified with aqueous ammonia (SG 0.880) and then filtered. The filtered residue was washed with ethyl acetate, then the washings and organic phase of the filtrate combined, washed with saturated brine and dried ($MgSO_4$). The ethyl acetate was evaporated under vacuum, the collidine removed by distillation under vacuum and the residue chromatographed on silica gel using ether:hexane (1:4) as eluent. The earlier fractions gave, after evaporation under vacuum, recovered tribromobenzene (42.5 g). The later fractions were evaporated under vacuum to afford the title compound as an oil (18.55 g); δ ($CDCl_3$): 7.07(2H,s), 7.22–7.26(2H,m), 7.42(1H,s), 8.42(1H,s), 8.47(1H,d). Found: C,40.49; H,2.17; N,4.19. $C_{11}H_7Br_2NO$ requires C,40.16; H,2.14; N,4.26%.

PREPARATION 7

3-Bromo-5-(3-pyridyloxy)benzaldehyde

A 1.3M solution of s-butyllithium in hexane (9.2 ml) was added dropwise to a stirred solution of 3-(3,5-dibromophenoxy)pyridine (Preparation 6; 3.29 g) in dry ether (100 ml) at –78° C., and the resulting mixture was stirred at this temperature for 15 minutes. N,N-dimethylformamide (2.2 g) was then added dropwise and this mixture stirred at the same temperature for 1 hour. Glacial acetic acid (1.6 ml) was next added and the reaction solution was allowed to warm to room temperature, washed sequentially with saturated aqueous sodium bicarbonate solution and water, then dried ($MgSO_4$). Evaporation under vacuum of the solvent gave an oil which was chromatographed on silica gel. Elution with dichloromethane first gave impurity which was followed by pure product. The product fractions were combined and evaporated under vacuum to give the title compound as an oil (1.80 g); δ ($CDCl_3$): 7.36–7.43 (4H,m), 7.76(1H,s), 8.45–8.50(2H,m), 9.90(1H,s). Found: C,51.76; H,2.89; N,5.04. $C_{12}H_8BrNO_2$ requires C,51.82; H,2.90; N,5.04%.

PREPARATION 8

3-Bromo-5-(3-pyridylmethyl)benzaldehyde

A 1.3M solution of s-butyllithium in hexane (27.7 ml) was added dropwise to a stirred suspension of 3-(3,5-dibromobenzyl)pyridine (Preparation 3; 9.81 g) in dry ether (300 ml) at –78° C. under an atmosphere of dry nitrogen. The resulting mixture was stirred at –78° C. for 15 minutes and then N,N-dimethylformamide (6.60 g) was added dropwise. This mixture was stirred at –78° C. for a further 30 minutes, allowed to warm to –20° C. and the glacial acetic acid (12 ml) was added. After 10 minutes, water (150 ml) was added and the organic phase separated. The aqueous layer was washed with ethyl acetate, then the combined organic solutions washed with saturated aqueous sodium bicarbonate solution and dried ($MgSO_4$). Evaporation under vacuum of the solvent gave a solid which was crystallised from ether-hexane to give the title compound (5.25 g), m.p. 97°–98° C. Found: C,56.21; H,3.71; N,5.19. $C_{13}H_{10}BrNO$ requires C,56.54; H,3.65; N,5.07%.

PREPARATION 9

3,5-Dibromobenzyl alcohol

Sodium borohydride (0.75 g) was added portionwise to a stirred suspension of 3,5-dibromobenzaldehyde (10.46 g) in methanol (50 ml) at 0° C. The mixture was stirred at 0° C. for 30 minutes, allowed to warm to room temperature and then its pH was adjusted to 2 using concentrated hydrochloric acid. Evaporation under vacuum provided a residue which was partitioned between ethyl acetate and water. The organic phase was washed with water, dried (MgSO$_4$), then evaporated under vacuum to furnish the title compound as a solid (10.0 g), m.p. 103°–104° C. Found: C,31.98; H,2.23. C$_7$H$_6$Br$_2$O requires C,31.61; H,2.77%.

PREPARATION 10

Ethyl 3-bromo-5-(3-pyridyloxy)cinnamate

Triethylphosphonoacetate (8.08 g) was added dropwise to a stirred suspension of sodium hydride (1.33 g of a 60% dispersion in mineral oil) in dry tetrahydrofuran (45 ml). The mixture was stirred for 30 minutes and then a solution of 3-bromo-5-(3-pyridyloxy)benzaldehyde (Preparation 7; 8.38 g) in dry tetrahydrofuran (45 ml) was added dropwise with vigorous stirring. After a further 15 minutes, the mixture was partitioned between ether and water. The organic phase was separated, washed with water and dried (MgSO$_4$). Evaporation of the solvent gave an oil which was chromatographed on silica gel. Elution with dichloromethane:methanol (100:1) gave the title compound as an oil (8.83 g); δ (CDCl$_3$): 1.31(3H,t,J=7.1 Hz), 4.24(2H,q,J= 7.1 Hz), 6.37(1H,d,J=16 Hz), 7.05(1H,s), 7.14(1H,s), 7.33(2H,m), 7.42(1H,s), 7.52(1H,d,J=16 Hz), 8.42–8.45(2H,m). Found: C,55.03; H,4.00; N,4.14. C$_{16}$H$_{14}$BrNO$_3$ requires C,55.19; H,4.05; N,4.02%.

The following two compounds were obtained from their respective benzaldehyde precursors and the appropriate phosphonate by procedures similar to that described in Preparation 10.

PREPARATION 11

Ethyl 3-bromo-5-(3-pyridylmethyl)cinnamate

From Preparation 8 and triethyl phosphonoacetate; m.p. 81°–83° C. Found: C,59.22; H,4.49; N,3.88. C$_{17}$H$_{16}$BrNO$_2$ requires C,58.97; H,4.66; N,4.05%.

PREPARATION 12 t-Butyl 3-bromo-5-(3-pyridylmethyl)cinnamate

From Preparation 8 and t-butyl dimethylphosphonoacetate; m.p. 97°–99°. Found: C,61.15; H,5.36; N,3.69. C$_{19}$H$_{20}$BrNO$_2$ requires C,60.97; H,5.39; N,3.74%.

PREPARATION 13

Ethyl 3-(2-ethoxycarbonylethenyl)-5-(3-pyridylmethyl)cinnamate

A stirred mixture of 3-(3,5-dibromobenzyl)pyridine (Preparation 3; 18.38 g), ethyl acrylate (16.86 g), palladium(II) acetate (640 mg), tri-o-tolylphosphine (1.69 g), triethylamine (17.05 g) and acetonitrile (40 ml) was heated under reflux under an atmosphere of dry nitrogen for 5 hours, and the volatile material was then removed under vacuum. The residue was partitioned between ethyl acetate and water, and the suspended material was removed by filtration. The aqueous phase was separated and extracted several times with ethyl acetate. The organic phase and extracts were combined, washed with water and dried (MgSO$_4$). Evaporation under vacuum gave an oil which was chromatographed on silica gel. Elution with dichloromethane gave recovered phosphine and further elution with dichloromethane-methanol (40:1) gave the required product (17.05 g), m.p. 94°–96° C. Found: C,72.11; H,6.30; N,3.76. C$_{22}$H$_{23}$NO$_4$ requires C,72.31; H,6.34; N,3.83%.

The following nine compounds were obtained from their respective bromoarene precursors and the appropriate excess of the required alkene by procedures similar to that described in Preparation 13. In several cases, dichloromethane was preferred to ethyl acetate as the partitioning solvent.

PREPARATION 14

Ethyl 3-(2-ethoxycarbonylethenyl-5-(4-pyridylmethyl)cinnamate

From Preparation 4 and ethyl acrylate; m.p. 103°–105° C. Found: C,71.78; H,6.24; N,3.72. C$_{24}$H$_{23}$NO$_4$; 0.25 H$_2$O requires C,71.43; H,6.40; N,3.79%.

PREPARATION 15

Ethyl 3-(2-ethoxycarbonylethenyl)5-[(α-hydroxy-α-methyl)-3-pyridylmethyl]cinnamate From Preparation 5 and ethyl acrylate; Rf 0.30 (SS 8); δ (CDCl$_3$): 1.32(6H,t), 2.00(3H,s), 2.66(1H,s), 4.26(4H,q), 6.44(2H,d), 7.23–7.28(1H,m), 7.53(1H,s), 7.58(2H,s), 7.63(2H,d), 7.72–7.76(1H,m), 8.49(1H,m), 8.68(1H,m).

PREPARATION 16

Ethyl 3-(2-ethoxycarbonylethenyl)-5-hydroxymethylcinnamate

From Preparation 9 and ethyl acrylate; m.p. 68°–69.5° C. Found: C,67.16; H,6.46. C$_{17}$H$_{20}$O$_5$ requires C,67.09; H,6.62%.

PREPARATION 17 t-Butyl 3-(3-methoxycarbonyl-2-propenyl)-5-(3-pyridylmethyl)cinnamate

Preparation 12 and methyl crotonate; m.p. 91°–93° C. Found: C,73.23; H,6.89; N,3.54. C$_{24}$H$_{27}$NO$_4$ requires C,73.26; H,6.92; N,3.56%.

PREPARATION 18 t-Butyl 3-(2-methoxycarbonyl-1-propenyl)-5-(3-pyridylmethyl)cinnamate

From Preparation 12 and methyl methacrylate; Rf 0.50 (SS 9). Found: C,73.23; H,6.66; N,3.39. C$_{24}$H$_{27}$NO$_4$ requires C,73.26; H,6.92; N,3.56%

PREPARATION 19

Ethyl 3-(2-cyanoethenyl)-5-(3-pyridylmethyl)cinnamate

From Preparation 11 and acrylonitrile; Rf 0.40 and 0.50 (SS 9); δ (CDCl$_3$): 1.32(3H,t,J=7.15 Hz), 4.00(2H,s), 4.25(2H,q,J=7.15 Hz), 5.88(1H,d,J=16.6 Hz), 6.42(1H,d,J= 16.0 Hz), 7.21–7.46(6H,m), 7.60(1H,d,J=16.0 Hz), 8.49–8.50(2H,m). The $^1$H nmr spectrum confirmed the presence of both the trans and cis cyanoalkenes.

PREPARATION 20

Ethyl 3-(2-phenylsulphonylethenyl)-5-(3-pyridylmethyl)cinnamate

From Preparation 11 and phenyl vinyl sulphone; m.p. 118°–120° C. Found: C,69.19; H,5.22; N,3.18. C$_{25}$H$_{23}$NO$_4$S requires C,69.26; H,5.35; N,3.23%.

PREPARATION 21

Ethyl 3-(3-phenylsulphonyl-1-propenyl)-5-(3-pyridylmethyl)cinnamate

From Preparation 11 and allyl phenyl sulphone; Rf 0.25 (SS 9); δ (CDCl$_3$): 1.35(3H,t), 3.93–3.98(4H,s+m), 4.15(2H, q), 6.07–6.17(1H,m), 6.32–6.41(2H,m), 7.09(1H,s), 7.22–7.28(3H,m), 7.43–7.68(4H,m), 7.88(2H,d), 8.50(2H, m).

PREPARATION 22 t-Butyl 3-(2-ethoxycarbonylethenyl)-5-(3-pyridyloxy)cinnamate

From Preparation 10 and t-butyl acrylate; m.p. 116°–118° C. Found: C,69.78; H,6.36; N,3.47. $C_{23}H_{25}NO_5$ requires C,69.85; H,6.37; N,3.54%.

PREPARATION 23

Ethyl 3-(2-ethoxycarbonylethenyl)-5-(1-imidazolylmethyl)cinnamate

Methylsulphonyl chloride (4.33 g) was added dropwise to a stirred solution of ethyl 3-(2-ethoxycarbonyl-1-ethenyl)-5-hydroxymethylcinnamate (Preparation 16; 10.46 g) and triethylamine (3.83 g) in dry dichloromethane (100 ml) at 0° C. The mixture was allowed to stand at room temperature for 1 hour and then washed with water and dried ($MgSO_4$). The solvent was evaporated under vacuum and the residue dissolved in acetone (100 ml). This solution was added over 20 minutes to a stirred mixture of imidazole (23.0 g), anhydrous sodium carbonate (7.29 g), sodium iodide (100 mg) and acetone (100 ml) at room temperature and the resulting mixture then heated under reflux for 10 hours, cooled and filtered. The solid thus obtained was washed with acetone, and the combined filtrate and washings were evaporated under vacuum. The residue partitioned between ethyl acetate and water, and the organic phase separated, washed with water and dried ($MgSO_4$). Evaporation under vacuum of the solvent gave a solid which was chromatographed on silica gel using a methanol in dichloromethane elution gradient (1 to 5% methanol). The later product fractions were combined and evaporated under vacuum and the residue crystallised from ether-hexane to afford the title compound (10.8 g), m.p. 116°–117.5° C. Found: C,67.84; H,6.31; N,7.98. $C_{20}H_{22}N_2O_4$ requires C,67.78; H,6.26; N,7.91%.

PREPARATION 24

Ethyl 3-[3-(2-ethoxycarbonylethyl)-5-(3-pyridylmethyl)phenyl]propanoate

10% Palladium on charcoal catalyst (1.30 g) was added portionwise to a stirred mixture of ethyl 3-(2-ethoxycarbonyl-1-ethenyl)-5-(3-pyridylmethyl)cinnamate Preparation 13; 13.0 g), ammonium formate (22.44 g), ethanol (100 ml) and tetrahydrofuran (100 ml) at room temperature under an atmosphere of dry nitrogen. The mixture was heated at 60° C. for 2 hours, then cooled and filtered. The filtrate was evaporated under vacuum and the residue partitioned between dichloromethane and water. The aqueous layer was separated and extracted with dichloromethane. The organic solutions were combined, dried ($MgSO_4$) and evaporated under vacuum to give the title compound as an oil (12.46 g); Rf 0.40 (SS 1); δ ($CDCl_3$): 1.20(6H,t,J=7.1 Hz), 2.55(4H,t, J=7.8 Hz), 2.86(4H,t,J=7.8 Hz), 3.89(2H,s), 4.09(4H,q,J=7.1 Hz), 6.84(2H,s), 6.89(1H,s), 7.16–7.20(1H,m), 7.41–7.45 (1H,m), 8.43–8.47(1H,m).

The following six compounds were obtained from their respective alkene precursors by procedures similar to that described in Preparation 24.

PREPARATION 25

Ethyl 3-[3-(2-ethoxycarbonylethyl-5-(4-pyridylmethyl)phenyl]propanoate

From Preparation 14; Rf 0.50 (SS 1); δ ($CDCl_3$): 1.21(6H, t), 2.56(4H,t), 2.87(4H,t), 3.91(2H,s), 4.09(4H,q), 6.85(2H, s), 6.93(1H,s), 7.11(2H,m), 8.49(2H,m).

PREPARATION 26

Ethyl 3-{3-(2-ethoxycarbonylethyl)-5-[(α-hydroxy-α-methyl)-3-pyridylmethyl]phenyl}propanoate From Preparation 15; Rf 0.30 (SS 8); δ ($CDCl_3$): 1.18–1.22(6H,m), 1.95(3H,s), 2.56(4H,t), 2.88(4H,t), 4.08(4H,q), 6.95(1H,s), 7.08(2H,s), 7.19–7.22(1H,m), 7.68–7.71(1H,m), 8.46(1H,m), 8.63(1H,m).

PREPARATION 27 t-Butyl 3-[3-(3-methoxycarbonyl-2-propyl)-5-(3-pyridylmethyl)phenyl]propanoate

From Preparation 17; Rf 0.45 (SS 1). Found: C,72.56; H,8.19; N,3.59. $C_{24}H_{31}NO_4$ requires C,72.51; H,7.86; N,3.52%.

PREPARATION 28 t-Butyl 3[3-(2-methoxycarbonyl-1-propyl)-5-(3-pyridylmethyl)phenyl]propanoate

From Preparation 18; Rf 0.45 (SS 1). Found: C,72.57; H,7.51; N,3.40. $C_{24}H_{31}NO_4$ requires C,72.51; H,7.86; N,3.52%.

PREPARATION 29 t-Butyl 3-[3-(2-ethoxycarbonylethyl)-5-(3-pyridyloxy)phenyl]propanoate

From Preparation 22; Rf 0.40 (SS 1). Found: C,68.82; H,7.26; N,3.45. $C_{23}H_{29}NO_5$ requires C,69.15; H,7.32; N,3.51%.

PREPARATION 30

Ethyl 3-[3-(2-ethoxycarbonylethyl-5-(1-imidazolylmethyl)phenyl]propanoate

From Preparation 23; Rf 0.20 (SS 1); δ ($CDCl_3$): 1.21(6H, t,J=7.1 Hz), 2.55(4H,t,J=7.7 Hz), 2.88(4H,t,J=7.7 Hz), 4.10(4H,q,J=7.1 Hz), 5.04(2H,s), 6.82(2H,s), 6.87(1H,s), 6.99(1H,s), 7.07(1H,s), 7.52(1H,s).

PREPARATION 31

3-[3-(2-Ethoxycarbonylethyl)-5-(3-pyridylmethyl)phenyl] propanoic acid

A solution of sodium hydroxide (1.66 g) in water (3 ml) was added to a solution of ethyl 3-[3-(2-ethoxycarbonylethyl)-5-(3-pyridylmethyl)phenyl] propanoate (Preparation 24; 15.27 g) in ethanol (25 ml) and the mixture was heated under reflux for 45 minutes. The resulting solution was evaporated under vacuum and the residue partitioned between water and ethyl acetate. The aqueous layer was washed with ethyl acetate and the combined organic solutions were dried ($MgSO_4$). Evaporation under vacuum gave recovered diester (4.18 g).

The aqueous phase was acidified to pH 4–5 with glacial acetic acid and the mixture was extracted several times with ethyl acetate. The combined extracts were washed with water and dried ($MgSO_4$). Evaporation under vacuum gave an oil which was chromatographed on silica gel, using dichloromethane: methanol:diethylamine (90:5:5) as eluent. Evaporation under vacuum of the product fractions gave an oil which was dissolved in ethyl acetate; this solution was washed with dilute aqueous acetic acid, followed by water, and then dried ($MgSO_4$). Evaporation under vacuum gave the title compound (6.13 g), m.p. 62°–64° C.; δ ($CDCl_3$): 1.20(3H,t,J=7.1 Hz), 2.54–2.64(4H,m), 2.85–2.93 (4H,m), 3.92(2H,s), 4.09(2H,q,J=7.1 Hz), 6.85 (1H,s), 6.89(1H,s), 6.93(1H,s), 7.23–7.27(1H,m), 7.53(1H,d,J=7.8 Hz), 8.42–8.48(2H,m).

The following three compounds were obtained from their respective diester precursors by procedures similar to that described in Preparation 31.

PREPARATION 32

3-[3-(2-Ethoxycarbonylethyl)-5-(4-pyridylmethyl)phenyl] propanoic acid

From Preparation 25; Rf 0.35 (SS 1); δ (CDCl$_3$): 1.20(3H, t), 2.54–2.65(4H,m), 2.87–2.93(4H,m), 3.91(2H,s), 4.10(2H,q), 6.84(1H,s), 6.90(1H,s), 6.93(1H,s), 7.12(2H,d), 8.39(2H,d).

PREPARATION 33

3-{3-(2-Ethoxycarbonylethyl)-5-[(α-hydroxy-α-methyl)-3-pyridylmethyl]phenyl}propanoic acid From Preparation 26; Rf 0.20 (SS 1); δ (CDCl$_3$): 1.20(3H, t), 1.90(3H,s), 2.50–2.60(4H,m), 2.83–2.90 (4H,m), 4.07(2H,q), 6.93(1H,s), 7.08(2H,s), 7.21–7.23 (1H,m), 7.78–7.81(1H,m), 8.33(1H,m), 8.51(1H,m).

PREPARATION 34

3-[3-(2-Ethoxycarbonylethyl)-5-(1-imidazolylmethyl)phenyl]propanoic acid

From Preparation 30; m.p. 103°–104.5° C. Found: C,65.20; H,6.55; N,8.43. C$_{18}$H$_{22}$N$_2$O$_4$ requires C,65.43; H,6.71; N,8.43%.

PREPARATION 35

3-[3-(2-Ethoxycarbonylethyl)-5-(3-pyridyloxy)phenyl]propanoic acid

A solution of t-butyl 3-[3-(2-ethoxycarbonylethyl)-5-(3-pyridyloxy)phenyl]propanoate (Preparation 29; 7.8 g) in dichloromethane (100 ml) was treated with trifluoroacetic acid (20 ml) and the resulting solution stirred at room temperature for 20 hours and then evaporated under vacuum. The residue was azeotroped twice with toluene, and then ether (ca 100 ml) and pyridine (ca 10 ml) were added sequentially. This mixture was washed with water and then the combined aqueous washings extracted with ethyl acetate. The organic solutions were combined, washed with water, dried (MgSO$_4$) and evaporated under vacuum to provide an oil, which crystallised on triturarion with an ether: hexane mixture to give the title compound (6.56 g), m.p. 85°–87° C. Found: C,66.67; H,6.04; N,3.90. C$_{19}$H$_{21}$NO$_5$ requires C,66.46; H,6.16; N,4.08%.

The following two compounds were obtained from their respective diester precursors by procedures similar to that described in Preparation 35.

PREPARATION 36

3-[3-(3-Methoxycarbonyl-2-propyl)-5-(3-pyridylmethyl)phenyl]propanoic acid

From Preparation 27; m.p. 82°–84° C. Found: C,70.40; H,7.05; N,4.01. C$_{20}$H$_{23}$NO$_4$ requires C,70.36; H,6.79; N,4.10%.

PREPARATION 37

3-[3-(2-Methoxycarbonyl-1-propyl)-5-(3-pyridylmethyl)phenyl]propanoic acid

From Preparation 28; m.p. 85°–87° C. Found: C,70.18; H,6.91; N,4.11. C$_{20}$H$_{23}$NO$_4$ requires C,70.36; H,6.79; N,4.10%.

PREPARATION 38 t-Butyl 3-[3-(2-carboxy-1-propyl)-5-(3-pyridylmethyl)phenyl]propanoate

A mixture of t-butyl 3-[3-(2-methoxycarbonyl-1-propyl)-5-(3-pyridylmethyl)phenyl]propanoate (Preparation 28; 2.84 g), 2N aqueous sodium hydroxide solution (4.3 ml) and 1,4-dioxane (13 ml) was stirred at room temperature for 2 hours, heated at 100° C. for 1.5 hours and then allowed to stand at room temperature for a further 18 hours. The solvent was evaporated under vacuum and the residue partitioned between ethyl acetate and water. The aqueous phase was separated, acidified with glacial acetic acid and extracted twice with dichloromethane, then the combined organic solutions dried (MgSO$_4$) and evaporated under vacuum. The residue was chromatographed on silica gel using a dichloromethane in methanol elution gradient (0 to 7% methanol), and the product fractions combined and evaporated under vacuum to give the title compound as a gum (1.88 g); Rf 0.60 (SS 7). Found: C,71.72; H,7.60; N,3.75. C$_{23}$H$_{29}$NO$_4$ requires C,72.03; H,7.62; N,3.65%.

PREPARATION 39

Ethyl 3-[3-(2-t-butoxycarbonylaminoethyl)-5-(3-pyridylmethyl)phenyl]propanoate

A solution of 3-[3-(2-ethoxycarbonylethyl)-5-(3-pyridylmethyl)phenyl]propanoic acid (Preparation 31; 4.89), diphenylphosphoryl azide (3.94 g) and triethylamine (1.45 g) in t-butanol (50 ml) was heated under reflux for 18 hours and then evaporated under vacuum. The residue was chromatographed on silica gel using dichloromethane:methanol (50:1) as eluent. After elution of some impurity, the product fractions were obtained; these were combined and evaporated under vacuum to give the title compound as an oil (3.60 g); Rf 0.50 (SS 1); δ (CDCl$_3$): 1.21(3H,t,J=7.1 Hz), 1.42(9H,s), 2.56(2H,t,J=7.8 Hz), 2.72(2H,t,J=7.1 Hz), 2.88(2H,t,J=7.8 Hz), 3.32(2H,m), 3.91(2H,s), 4.09(2H,t,J=7.1 Hz), 4.53(1H, br), 6.85(1H,s), 6.86(1H,s), 6.89(1H,s), 7.17–7.21 (1H,m), 7.43–7.45 (1H,m), 8.44–8.48(2H,m).

The following five compounds were obtained from their respective carboxylic acid precursors by procedures similar to that described in Preparation 39.

PREPARATION 40

Ethyl 3-[3-(2-t-butoxycarbonylaminoethyl)-5-(4-pyridylmethyl)phenyl]propanoate

From Preparation 32; Rf 0.50 (SS 1); δ (CDCl$_3$): 1.21(3H, t), 1.42(9H,s), 2.57(2H,t), 2.73(2H,t), 2.88(2H,t), 3.28–3.36(2H,m), 3.90(2H,s), 4.08(2H,q), 6.84(1H,s), 6.86(1H,s), 6.91(1H,s), 7.08(2H,d), 8.47(2H,d).

PREPARATION 41

Ethyl 3-[3-(2-t-butoxycarbonylaminoethyl)-5-(1-imidazolylmethyl)phenyl]propanoate From Preparation 34; Rf 0.40 (SS 2). Found: C,65.42; H,7.53; N,10.36. C$_{22}$H$_{31}$N$_3$O$_4$ requires C,65.81; H,7.78; N,10.47%.

PREPARATION 42

Ethyl 3-[3-(2-t-butoxycarbonylaminoethyl)-5-(3-pyridyloxy)phenyl]propanoate

From Preparation 35; Rf 0.60 (SS 2); δ (CDCl$_3$): 1.21(3H, t,J=7.1 Hz), 1.41(9H,s), 2.57(2H,t,J=7.7 Hz), 2.73(2H,m), 2.89(2H,t,J=7.7 Hz), 3.30–3.35(2H,m), 4.10(2H,q,J=7.1 Hz), 6.68(1H,s), 6.71(1H,s), 6.81(1H,s), 7.25–7.26 (2H,m), 8.35–8.36(2H,m).

PREPARATION 43

Methyl 3-[3-(2-t-butoxycarbonylaminoethyl)-5-(3-pyridylmethyl)phenyl]butanoate

From Preparation 36; Rf 0.70 (SS 2); δ (CDCl$_3$): 1.25(3H, d,J=6 Hz), 1.42(9H,s), 2.50–2.55(2H,m), 2.70–2.75 (2H,m), 3.58(3H,s), 3.92(2H,s), 4.50(1H,s), 6.83(1H,s), 6.89(2H,s), 7.18–7.22(1H,m), 7.45(1H,d,J=7.4 Hz), 8.45–8.48(2H,m).

PREPARATION 44

Methyl 2-[3-(2-t-butoxycarbonylaminoethyl)-5-(3pyridylmethyl)benzyl]propanoate

From Preparation 37; Rf 0.75 (SS 2); δ (CDCl$_3$): 1.19(3H, d,J=6.3 Hz), 1.42(9H,s), 2.55–2.75(4H,m), 2.90–2.98 (1H, m), 3.28–3.32(2H,m), 3.58(3H,s), 3.91(2H,), 4.50(1H,s), 6.82(1H,s), 6.84(2H,s), 7.18–7.22(1H,m), 7.43(1H,d,J=7.4 Hz), 8.47(2H,m).

PREPARATION 45 t-Butyl 3-[3-(2-benzyloxycarbonylamino-1-propyl)-5-(3-pyridylmethyl)phenyl]propanoate A solution of t-butyl 3-[3-(2-carboxy-1-propyl)-5-(3-pyridylmethyl)phenyl]propanoate (Preparation 38; 1.84 g), diphenylphosphoryl azide (1.45 g) and triethylamine (0.53 g) in dry 1,4-dioxane (12 ml) was heated at 100° C. for 45 minutes. Benzyl alcohol (0.78 g) was then added and the resulting solution heated under reflux for 18 hours and then evaporated under vacuum. The residue was chromatographed on silica gel using dichloromethane:methanol (95:5) as eluent, then the product fractions combined and evaporated under vacuum to give the title compound as an oil (2.30 g); Rf 0.25 (SS 1); δ (CDCl$_3$): 1.08(3H,d), 1.40(9H, s), 2.48(2H,t), 2.55–2.63(2H,m), 2.81(2H,t), 2.89(2H,s), 3.89–3.95(1H,m), 5.07(2H,s), 6.82(1H,s), 6.87(2H,s), 7.12–7.18(1H,m), 7.27–7.42(6H,m), 8.40–8.45(2H,m).

The following compound was obtained from its carboxylic acid precursor by a procedure similar to that described in Preparation 45.

PREPARATION 46

Ethyl 3-{3-(2-benzyloxycarbonylaminoethyl)-5-[(α-hydroxy-α-methyl)- 3-pyridylmethyl]phenyl}propanoate From Preparation 33; Rf 0.50 (SS 1); δ (CDCl$_3$): 1.11(3H, t), 1.92(3H,s), 2.56(2H,t), 2.76(2H,t), 2.88(2H,t), 3.41(2H, m), 3.70(1H,s), 4.08(2H,q), 5.07(2H,s), 6.91(1H,s), 7.09(1H,s), 7.11(1H,s), 7.20–7.36 (6H,m), 7.71(1H,s), 7.43(1H,d), 8.62(1H,d).

PREPARATION 47

Ethyl 3-[3-(2-aminoethyl)-5-(3-pyridylmethyl)phenyl]propanoate

A solution of ethyl 3-[3-(2-t-butoxycarbonylaminoethyl)-5(3-pyridylmethyl)phenyl]propanoate (Preparation 39; 4.10 g) and trifluoroacetic acid (.4.1 ml) in dry dichloromethane (41 ml) was stirred for 6 hours, additional 4.1 ml portions of trifluoroacetic acid being added after 2 and 5 hours. The solution was evaporated under vacuum and the residue basified with aqueous sodium bicarbonate solution. The mixture was extracted several times with dichloromethane and the combined extracts were dried (MgSO$_4$) and evaporated under vacuum. Water (ca 75 ml) was added and this mixture was acidified to pH 4 with glacial acetic acid and then extracted several times with ethyl acetate. The aqueous layer was basified with aqueous ammonia solution (SG 0.880) and extracted several times with dichloromethane. The combined dichloromethane extracts were washed with water, dried (MgSO$_4$) and evaporated under vacuum to give the title compound as an oil (2.24 g); Rf 0.10 (SS 2); δ (CDCl$_3$): 1.07(2H,br), 1.20(3H,t,J=7.1 Hz), 2.56(2H,t,J=7.8 Hz), 2.66(2H,t,J=6.9 Hz), 2.85–2.93(4H,m), 3.90(2H,s), 4.09(2H,q,J=7.1 Hz), 6.84 (2H,s), 6.88(1H,s), 7.16–7.20 (1H,m), 7.43(1H,d,J=7.8 Hz), 8.43–8.47(2H,m).

The following five compounds were obtained from their respective carbamate precursors by procedures similar to that described in Preparation 47.

PREPARATION 48

Ethyl 3-[3-(2-aminoethyl)-5-(4-pyridylmethyl)phenyl]propanoate

From Preparation 40; Rf 0.50 (SS 10); δ (CDCl$_3$): 1.21(3H,t), 1.34(2H,s), 2.58(2H,t), 2.68(2H,t), 3.87–3.93 (4H,m), 3.90(2H,s), 4.09(2H,q), 6.84(2H,s), 6.90(1H,s), 7.08(2H,d), 8.49(2H,d).

PREPARATION 49

Ethyl 3-[3-(2-aminoethyl)-5-(1-imidazolylmethyl)phenyl] propanoate

From Preparation 41; Rf 0.10 (SS 2); δ (CDCl$_3$): 1.20(3H, t,J=7.1 Hz), 2.57(2H,t,J=7.7 Hz), 2.67(2H,t,J=6.8 Hz), 2.85–2.95(4H,m), 4.08(2H,q,J=7.1 Hz), 5.06(2H,s), 6.82(1H,s), 6.83(1H,s), 6.90(1H,s), 6.99(1H,s), 7.08(1H,s), 7.53(1H,s).

PREPARATION 50

Ethyl 3-[3-(2-aminoethyl)-5-(3-pyridyloxy)phenyl]propanoate

From Preparation 42; Rf 0.10 (SS 2); δ (CDCl$_3$): 1.21(3H, t,J=7.1 Hz), 2.58(2H,t,J=7.7 Hz), 2.68(2H,t,J=6.8 Hz), 2.87–2.96(4H,m), 4.10(2H,q,J=7.1 Hz), 6.70(2H,s), 6.82(1H,s), 7.25–7.26(2H,m), 8.33–8.37 (2H,m).

PREPARATION 51

Methyl 3-[3-(2-aminoethyl)-5-(pyridylmethyl)phenyl]butanoate

From Preparation 43; Rf 0.10 (SS 2); δ (CDCl$_3$): 1.08(3H, d,J=6.8 Hz), 2.53(2H,m), 2.67(2H,t,J=6.7 Hz), 2.91(2H,t,J= 6.7 Hz), 3.22(1H,q,J=6.8 Hz), 3.58(3H,s), 3.92(2H,s), 6.83(1H,s), 6.87(1H,s), 6.90(1H,s), 7.19–7.21 (1H,m), 7.44–7.46(1H,m), 8.44–8.48(2H,m).

PREPARATION 52

Methyl 2-[3-(2-aminoethyl)-5-(3-pyridylmethyl)benzyl] propanoate

From Preparation 44; Rf 0.10 (SS 2); δ (CDCl$_3$): 1.10–1.13(3H,m), 1.31(2H,br), 2.55–2.75(4H,m), 2.86–2.93 (3H,m), 3.58(3H,s), 3.90(2H,s), 6.80(1H,s), 6.84(2H,s), 7.16–7.21(1H,m), 7.42–7.44(1H,m), 8.44–8.47 (2H,m).

PREPARATION 53 t-Butyl 3-[3-(2-amino-1-propyl)-5-(3-pyridylmethyl)phenylpropanoate

A stirred mixture of t-butyl 3-[3-(2-benzyloxycarbonylamino- 1-propyl)-5-(3-pyridylmethyl)phenyl]propanoate (Preparation 45; 2.30 g), ammonium formate (2.96 g), 10% palladium on charcoal catalyst (0.23 g), methanol (10 ml) and tetrahydrofuran (10 ml) was heated under reflux for 2 hours, then allowed to cool and filtered. The residue was washed with methanol, the combined filtrate and washings evaporated under vacuum and the residue partitioned between dichloromethane and water. The aqueous phase was basified with aqueous ammonia solution (SG 0.880) and extracted with dichloromethane. The organic solutions were combined, dried ($MgSO_4$) and evaporated under vacuum to give an oil which was chromatographed on silica gel using a methanol in dichloromethane elution gradient (0 to 10% methanol). The product fractions were combined and evaporated under vacuum to give the title compound as an oil (0.98 g); Rf 0.10 (SS 2); δ ($CDCl_3$): 1.10(3H,d,J=6.3 Hz), 1.38(9H,s), 1.96(2H,br), 2.44–2.51 (3H,m), 2.61–2.68(1H, m), 2.83(2H,t,J=7.7 Hz), 3.09–3.18 (1H,m), 3.90(2H,s), 6.85(1H,s), 6.86(1H,s), 6.88(1H,s), 7.16–7.20(1H,m) 7.44(1H,d,J=7.8 Hz), 8.41–8.43 (1H,m), 8.47(1H,m).

The following compound was obtained from its carbamate precursor by a procedure similar to that described in Preparation 53.

PREPARATION 54

Ethyl 3-{3-(2-aminoethyl)-5-[(α-hydroxy-α-methyl)-3-pyridylmethyl]phenyl}propanoate From Preparation 46; Rf 0.30 (SS 10); δ ($CDCl_3$): 1.20(3H,t), 1.91(3H,s), 2.07(2H,br). 2.57(2H,t), 2.66(2H,t), 2.81–2.90(4H,m), 4.08(2H,q), 6.90(1H,s), 7.07(2H,s), 7.18–7.22(1H,m), 7.69(1H,m), 8.41(1H,m), 8.60(1H,m).

PREPARATION 55

Ethyl 3-[3-(3-amino-1-propyl)-5-(3-pyridylmethyl)phenyl] propanoate

Sodium borohydride (2.30 g) was added portionwise with vigorous stirring to a solution of ethyl 3-(2-cyanoethenyl)-5-(3-pyridylmethyl)cinnamate (Preparation 19; 2.0 g) and cobalt(II) chloride hexahydrate (4.48 g) in ethanol (150 ml) at 0° C. The mixture was stirred for 2 hours, carefully acidified to pH 2 with concentrated hydrochloric acid, stirred for a further 10 minutes, basified with concentrated aqueous ammonia solution (SG 0.880) and then filtered. The filtered material was washed with ethyl acetate, the combined filtrate and washings washed with water, and the combined aqueous washings then extracted three times with dichloromethane. The organic extracts were combined, dried ($MgSO_4$) and evaporated under vacuum to give a gum, which was chromatographed on silica gel. The column was eluted with a methanol in dichloromethane elution gradient (1% to 5% methanol), followed by a dichloromethane:methanol:aqueous ammonia (SG 0.880) elution gradient (94:5:1 to 90:9:1). The product fractions were combined and evaporated under vacuum to give the title compound as a gum (0.825 g); Rf 0.25 (SS 2); δ ($CDCl_3$): 1.20(3H,t,J=7.1 Hz), 1.70–1.77 (4H,m), 2.54–2.60(4H,m), 2.70(2H,t,J=7.0 Hz), 2.87(2H,t,J=7.8 Hz), 3.90(2H,s), 4.09(2H,q,J=7.1 Hz), 6.83(2H,s), 6.88(1H,s), 7.18–7.22(1H,m), 7.43–7.46 (1H, m), 8.43–8.48(2H,m).

Biological activity

The following Table illustrates the dual in vitro activities for a range of the compounds of the invention.

| EXAMPLE NUMBER | $TxA_2$ SYNTHETASE INHIBITORY ACTIVITY: $IC_{50}(M)$ | $TxA_2$ ANTAGONIST ACTIVITY: $pA_2$ |
|---|---|---|
| 48 | $3.9 \times 10^{-8}$ | 9.39 |
| 49 | $4.9 \times 10^{-8}$ | 9.44 |
| 61 | $3.8 \times 10^{-8}$ | 9.06 |
| 62 | $3.7 \times 10^{-8}$ | 9.40 |
| 67 | $6.1 \times 10^{-8}$ | 9.07 |
| 82 | $5.0 \times 10^{-8}$ | 9.12 |
| 83 | $5.3 \times 10^{-8}$ | 10.01 |
| 84 | $4.4 \times 10^{-8}$ | 9.73 |
| 85 | $3.8 \times 10^{-8}$ | 10.16 |

Safety profile

Several of the compounds of the invention have been tested orally in conscious dogs at doses of up to 10 mg/Kg. No signs of adverse acute toxicity were observed in this dose range.

We claim:

1. A compound of formula:

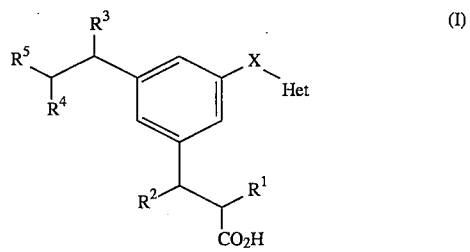

or a ($C_1$–$C_4$)alkyl ester thereof, or a pharmaceutically acceptable salt of either, wherein $R^1$, $R^2$, $R^3$ and $R^4$ are each independently selected from H or $C_1$–$C_4$ alkyl;

$R^5$ is $(CH_2)_m SO_2 R^6$, $(CH_2)_m NHSO_2 R^6$ or $(CH_2)_m NHCOR^7$;

$R^6$ and $R^7$ are to $C_1$–$C_6$ alkyl, $C_1$–$C_3$ perfluoroalkyl$(CH_2)_n$, $C_3$–$C_6$ cycloalkyl$(CH_2)_n$, aryl$(CH_2)_n$ or heteroaryl$(CH_2)_n$; or $R^6$ is $NR^8 R^9$;

$R^8$ is H or $C_1$–$C_4$ alkyl;

$R^9$ is $C_1$–$C_6$ alkyl, $C_3$–$C_6$ cycloalkyl$(CH_2)_n$, aryl$(CH_2)_n$ or heteroaryl$(CH_2)_n$;

X is $CH_2$, $CHCH_3$, $C(OH)CH_3$, $C=CH_2$ or O;

m is 0 or 1;

n is 0, 1, 2 or 3; and

Het is 3- or 4-pyridyl.

2. A compound as claimed in claim 1 wherein $R^1$, $R^2$, $R^3$ and $R^4$ are each independently selected from H or methyl; $R^5$ is $CH_2 SO_2$phenyl, $SO_2$phenyl, $NHCOCH_2 CH(CH_3)_2$, NHCOphenyl, $CH_2 NHSO_2$(4-chlorophenyl) or $NHSO_2 R^6$; $R^6$ is $C_1$–$C_5$ alkyl, $CH_2 CF_3$, cyclohexyl, phenyl, 4-fluorophenyl, 4-chlorophenyl, 4-bromophenyl, 4-methylphenyl, 2-furyl or $NR^8 R^9$; $R^8$ is H, methyl or ethyl; and $R^9$ is methyl, ethyl or 4-chlorophenyl.

3. A compound as claimed in claim 2 wherein $R^1$, $R^2$, $R^3$ and $R^4$ are H; $R^5$ is $NHSO_2 R^6$; $R^6$ is phenyl, 4-chlorophenyl or 4-bromophenyl; and Het is 3-pyridyl.

4. A compound as claimed in claim 1 wherein the $C_1$–$C_4$ alkyl ester is a methyl, ethyl or t-butyl ester.

5. A pharmaceutical composition comprising a compound of formula (I) or a ($C_1$–$C_4$)alkyl ester thereof, or a pharmaceutically acceptable salt of either, as claimed in claim 1, together with a pharmaceutically acceptable diluent or carrier.

6. A compound of formula:
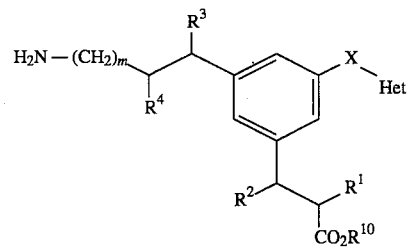
(III)
wherein either X is $CH_2$, $C(OH)CH_3$ or O and Het is 3- or 4-pyridyl, $R^{10}$ is $C_1$–$C_4$ alkyl, and $R^1$, $R^2$, $R^3$, $R^4$ and m are as defined in claim 1.
7. A compound of formula:
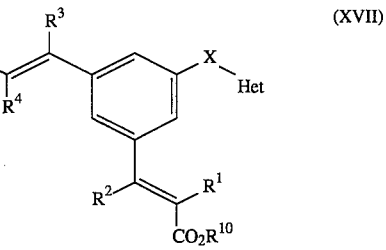
(XVII)
wherein either X is $CH_2$, $C(OH)CH_3$ or O and Het is 3- or 4-pyridyl, $R^{10}$ is $C_1$–$C_4$ alkyl, and $R^1$, $R^2$, $R^3$, $R^4$, $R^6$ and m are as defined in claim 1.
* * * * *